(12) United States Patent
Wang et al.

(10) Patent No.: US 9,801,600 B2
(45) Date of Patent: Oct. 31, 2017

(54) X-RAY PHASE-CONTRAST IMAGING

(71) Applicants: Ge Wang, Loudonville, NY (US); Yan Xi, Troy, NY (US); Wenxiang Cong, Albany, NY (US)

(72) Inventors: Ge Wang, Loudonville, NY (US); Yan Xi, Troy, NY (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 92 days.

(21) Appl. No.: 14/943,157

(22) Filed: Nov. 17, 2015

(65) Prior Publication Data

US 2016/0135769 A1    May 19, 2016

Related U.S. Application Data

(60) Provisional application No. 62/080,560, filed on Nov. 17, 2014.

(51) Int. Cl.
| | |
|---|---|
| *H01J 5/16* | (2006.01) |
| *A61B 6/00* | (2006.01) |
| *A61B 6/03* | (2006.01) |
| *G06T 11/00* | (2006.01) |
| *G21K 1/02* | (2006.01) |

(52) U.S. Cl.
CPC ............. *A61B 6/484* (2013.01); *A61B 6/032* (2013.01); *A61B 6/4035* (2013.01); *A61B 6/4233* (2013.01); *A61B 6/4291* (2013.01); *A61B 6/5205* (2013.01); *G06T 11/005* (2013.01); *G21K 1/025* (2013.01); *G21K 2207/005* (2013.01)

(58) Field of Classification Search
CPC .......... A61B 6/23; A61B 6/502; G21K 1/067; G01N 23/046; G01N 23/20075
USPC ......................................... 378/5, 19, 62, 156
See application file for complete search history.

(56) References Cited

U.S. PATENT DOCUMENTS

| | | | | |
|---|---|---|---|---|
| 2013/0028378 A1* | 1/2013 | Stutman | ................. | G01N 23/04 378/62 |
| 2015/0092914 A1* | 4/2015 | Anton | .............. | G01N 23/20075 378/36 |
| 2015/0279496 A1* | 10/2015 | Bauer | .................... | A61B 6/032 378/19 |
| 2016/0022235 A1* | 1/2016 | Ning | ...................... | A61B 6/032 378/4 |

OTHER PUBLICATIONS

Cohen-Sabban, Y. et al., "Aberration-free Nonparaxial Self-Imaging,"*J. Opt. Soc. Am.*, 73(5), pp. 707-719, (1983).

(Continued)

*Primary Examiner* — Don Wong
(74) *Attorney, Agent, or Firm* — Saliwanchik, Lloyd & Eisenschenk

(57) ABSTRACT

Systems and methods for X-ray phase-contrast imaging (PCI) are provided. A quasi-periodic phase grating can be positioned between an object being imaged and a detector. An analyzer grating can be disposed between the phase grating and the detector. Second-order approximation models for X-ray phase retrieval using paraxial Fresnel-Kirchhoff diffraction theory are also provided. An iterative method can be used to reconstruct a phase-contrast image or a dark-field image.

16 Claims, 23 Drawing Sheets

(56) References Cited

OTHER PUBLICATIONS

Guigay, J.P. "Fourier-Transform Analysis of Fresnel Diffraction Patterns and in-Line Holograms," *Optik*, 49(1), pp. 121-125, (1977).

Momose, Atsushi et al., "Phase-contrast X-ray Computed Tomography for Observing Biological Soft Tissues," *Nature medicine*, 2(4), pp. 473-475, (1996).

Montgomery, W.D. "Self-Imaging Objects of Infinite Aperture," *J. Opt. Soc. Am.* 57(6), pp. 772-778, (1967).

Patorski, Krzysztof "The Self-Imaging Phenomenon and Its Applications," *Progress in Optics*, 27, pp. 1-108, (1989).

Soto, Marcos et al. "Improved Phase Imaging from Intensity Measurements in Multiple Planes," *Applied Optics*, 46(33), pp. 7978-7981, (2007).

Teague, M.R. "Deterministic Phase Retrieval: a Green's Function Solution," *Journal of the Optical Society of America*, 73(11), pp. 1434-1441, (1983).

Teague, M.R. "Irradiance Moments: Their Propagation and Use for Unique Retrieval of Phase," *Journal of the Optical Society of America*, 72(9), 1199-1209, (1982).

Wang, Ge et al. "An Outlook on X-ray CT Research and Development," *Medical physics*, 35(3), pp. 1051-1064, (2008).

Wen, Jianming et al. "The Talbot Effect: Recent Advances in Classical Optics, Nonlinear Optics, and Quantum Optics," *Advances in Optics and Photonics*, 5(1), pp. 83-130, 2013.

Azaña, José et al. "Angular Talbot effect," *Physical Review Letters*, vol. 112, No. 21, pp. 213902-1-213902-5, 2014.

Berry, M.V. et al. "Integer, fractional and fractal Talbot effects," *Journal of modern optics*, vol. 43, No. 10, pp. 2139-2164, 1996.

Bravin, Alberto et al. "High-resolution CT by diffraction-enhanced xray imaging: mapping of breast tissue samples and comparison with their histo-pathology," *Phys. Med. Biol.* vol. 52, No. 8, pp. 2197-2211, 2007.

Bravin, Alberto et al. "X-ray phase-contrast imaging: from preclinical applications towards clinics," *Physics in Medicine and Biology*, vol. 58, No. 1, pp. R1-R35, 2013.

Chapman, D. et al. "Diffraction enhanced x-ray imaging," *Physics in medicine and biology*, vol. 42, No. 11, pp. 2015-2025, 1997.

Chou, Cheng-Ying et al. "Image reconstruction in quantitative X-ray phase-contrast imaging employing multiple measurements," *Optics Express*, vol. 15, No. 16, pp. 10002-10025, 2007.

Cohen-Sabban, Y. et al. "Aberration-free nonparaxial self-imaging," *Journal of the Optical Society of America*, vol. 73, No. 5, 1983, Abstract only.

Cong, Wenxiang et al. "Differential phase-contrast interior tomography," *Physics in Medicine and Biology*, vol. 57, No. 10, pp. 2905-2914, 2012.

Cong, Wenxiang et al. "Higher-order phase shift reconstruction approach," *Medical Physics*, vol. 37, No. 10, 5238-5242, 2010.

David, C. et al. "Fabrication of diffraction gratings for hard X-ray phase contrast imaging," *Microelectronic Engineering*, vol. 84, No. 5-8, pp. 1172-1177, 2007.

Davis, T.J. et al., "Phase-contrast imaging of weakly absorbing materials using hard X-rays," *Nature*, vol. 373, No. 6515, pp. 595-598, 1995.

Fitzgerald, Richard "Phase-sensitive x-ray imaging," *Physics Today*, vol. 53, No. 7, pp. 23-26, 2000.

Guigay, J.P. et al. "Mixed transfer function and transport of intensity approach for phase retrieval in the Fresnel region," *Optics Letters*, vol. 32, No. 12, pp. 1617-1619, 2007.

Langer, Max et al. "Quantitative comparison of direct phase retrieval algorithms in in-line phase tomography," *Medical Physics*, vol. 35, No. 10, pp. 4556-4566, 2008.

Lewis, R.A. "Medical phase contrast x-ray imaging: current status and future prospects," *Physics in medicine and biology*, vol. 49, No. 16, pp. 3573-3583, 2004.

Momose, Atsushi et al. "Demonstration of X-ray Talbot interferometry," *Japanese journal of applied physics*, vol. 42, No. 7B, pp. L866-L868, 2003.

Momose, Atsushi et al. "Phase-contrast X-ray computed tomography for observing biological soft tissues," *Nature medicine*, vol. 2, No. 4, 1996, Abstract only.

Momose, Atsushi et al. "X-ray phase imaging: from synchrotron to hospital," *Philosophical Transactions of the Royal Society A: Mathematical, Physical and Engineering Sciences*, vol. 372, No. 2010, pp. 1-7, 2014.

Montgomery, W.D. "Self-Imaging Objects of Infinite Aperture," *Journal of the Optical Society of America*, vol. 57, No. 6, 1967, Abstract only.

Patorski, Krzysztof, "I The Self-Imaging Phenomenon and its Applications," *Progress in optics*, vol. 27, 1989, Abstract only.

Pfeiffer, Franz et al. "Grating-based X-ray phase contrast for biomedical imaging applications," *Zeitschrift Fur Medizinische Physik*, vol. 23, No. 3, pp. 176-185, 2013.

Pfeiffer, Franz et al. "Phase retrieval and differential phase-contrast imaging with low-brilliance X-ray sources," *Nature physics*, vol. 2, No. 4, pp. 258-261, 2006.

Revol, Vincent et al. "X-ray interferometer with bent gratings: Towards larger fields of view," *Nuclear Instruments and Methods in Physics Research, Sect. A*, vol. 648, pp. S302-S305, 2011.

Silver, Samuel et al. "The external field produced by a slot in an infinite circular cylinder," *Journal of Applied Physics*, vol. 21, No. 2, pp. 153-158, 1950.

Soto, Marcos et al. "Improved phase imaging from intensity measurements in multiple planes," *Applied Optics*, vol. 46, No. 33, 2007, Abstract only.

Stampanoni, Marco et al. "The first analysis and clinical evaluation of native breast tissue using differential phase-contrast mammography," *Investigative radiology*, vol. 46, No. 12, pp. 801-806, 2011.

Takeda, Tohoru et al. "Human Carcinoma: Early Experience with Phase-Contrast X-ray CT with Synchrotron Radiation—Comparative Specimen Study with Optical Microscopy 1," *Radiology*, vol. 214, No. 1, pp. 298-301, 2000.

Tanaka, Junji et al. "Cadaveric and in vivo human joint imaging based on differential phase contrast by X-ray Talbot-Lau interferometry," *Zeitschrift für Medizinische Physik*, vol. 23, No. 3, pp. 222-227, 2013.

Tapfer, Arne et al. "Experimental results from a preclinical X-ray phase-contrast CT scanner," *Proceedings of the National Academy of Sciences*, vol. 109, No. 39, pp. 15691-15696, 2012.

Tapfer, Arne et al. "Three-dimensional imaging of whole mouse models: comparing nondestructive X-ray phase-contrast micro-CT with cryotome-based planar cpi-illumination imaging," *Journal of Microscopy*, vol. 253, No. 1, pp. 24-30, 2014.

Teague, Michael Reed, "Deterministic Phase Retrieval—a Green-Function Solution," *Journal of the Optical Society of America*, vol. 73, No. 11, 1983, Abstract only.

Teague, Michael Reed, "Irradiance Moments—Their Propagation and Use for Unique Retrieval of Phase," *Journal of the Optical Society of America*, vol. 72, No. 9, 1982, Abstract only.

Thüring, Thomas, "Compact X-ray grating interferometry for phase and dark-field computed tomography in the diagnostic energy range," *Diss. Diss., ETH Zürich*, Nr. 21321, pp. i-170, 2013.

Thüring, T. et al. "X-ray phasecontrast imaging at 100 keV on a conventional source," *Scientific Reports*, vol. 4, pp. 1-4, 2014.

Wang, GE et al. "An outlook on x-ray CT research and development," *Medical physics*, vol. 35, No. 3, 2008, Abstract only.

Weitkamp, Timm et al. "X-ray phase imaging with a grating interferometer," *Optics express*, vol. 13, No. 16, pp. 6296-6304, 2005.

Weitkamp, Timm et al. "X-ray phase radiography and tomography of soft tissue using grating interferometry," *European Journal of Radiology*, vol. 68, No. 3, pp. S13-S17, 2008.

Wen, Jianming et al. "The Talbot effect: recent advances in classical optics, nonlinear optics, and quantum optics," *Advances in Optics and Photonics*, vol. 5, No. 1, 2013, Abstract only.

Wu, Xizenf et al., "A general theoretical formalism for X-ray phase contrast imaging," *Journal of X-Ray Science and Technology*, vol. 11, No. 1, pp. 33-42, 2003.

Wu, Xizeng et al. "Clarification of aspects in in-line phase-sensitive x-ray imaging," *Medical Physics*, vol. 34, No. 2, pp. 737-743, 2007.

(56) References Cited

OTHER PUBLICATIONS

Wilkins, S.W. et al. "Phase contrast imaging using polychromatic hard X-rays," *Nature*, vol. 384, No. 6607, pp. 335-338, 1996.
Yang, Jiansheng et al. "High-order total variation minimization for interior tomography," *Inverse Problems*, vol. 26, No. 3, pp. 1-30, 2010.
Yu, Hengyong et al. "Compressed sensing based interior tomography," *Physics in Medicine and Biology*, vol. 54, No. 9, pp. 2791-2805, 2009.
Zhu, Peiping et al. "Low-dose, simple, and fast grating-based X-ray phase-contrast imaging," *Proceedings of the National Academy of Sciences*, vol. 107, No. 31, pp. 13576-13581, 2010.

* cited by examiner

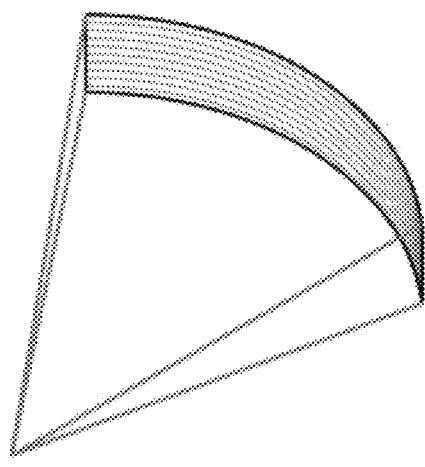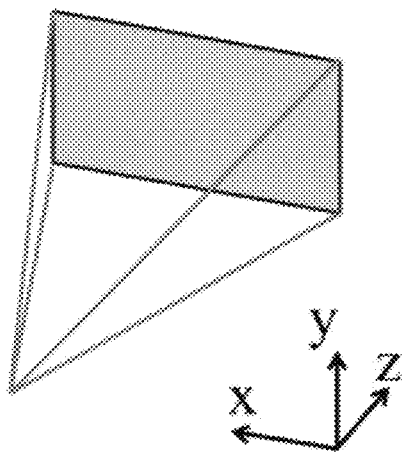
FIG. 1A
FIG. 1B

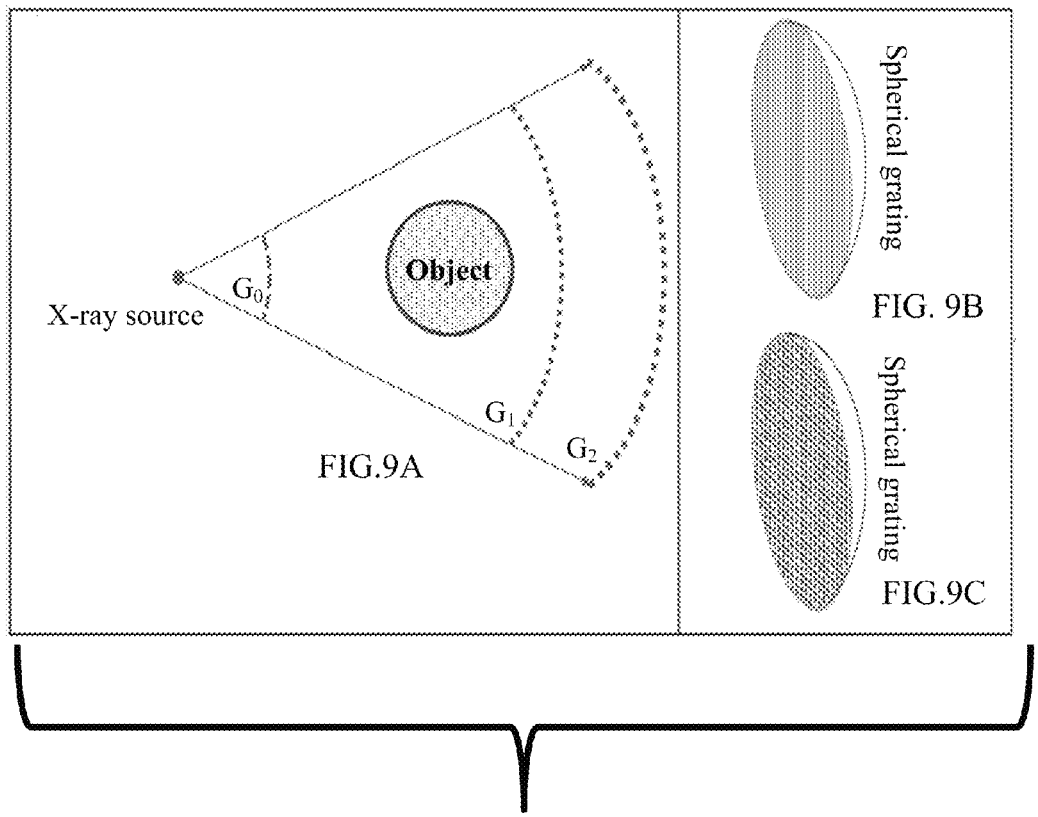
FIGS. 9A-9C
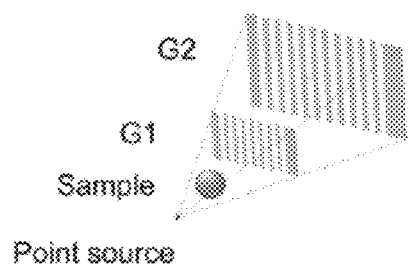 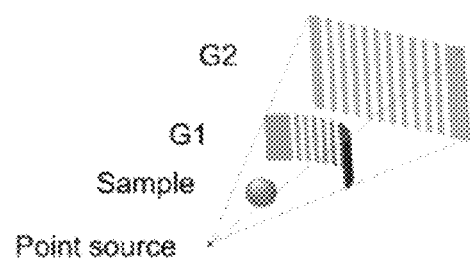
FIG. 10A　　　　FIG. 10B

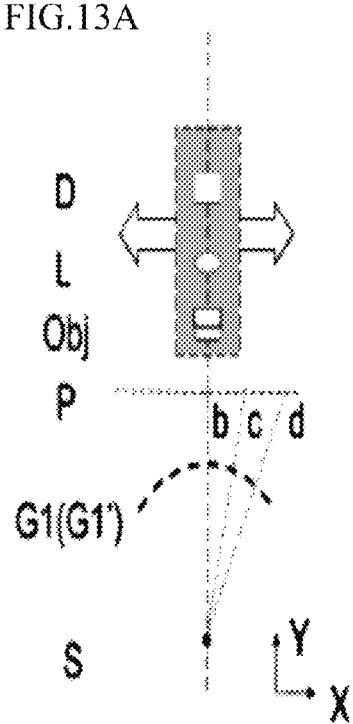
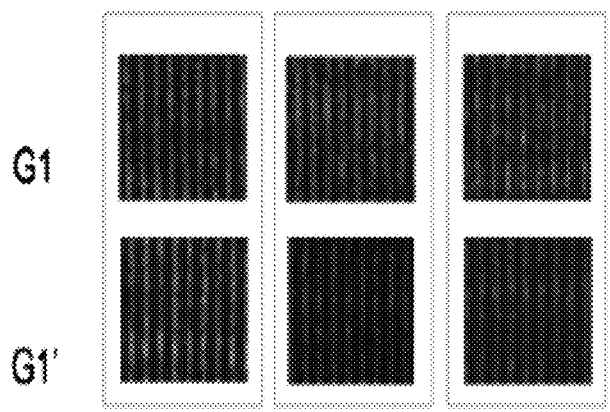
FIG.13A  FIG.13B  FIG.13C  FIG.13D

X-RAY PHASE-CONTRAST IMAGING

CROSS-REFERENCE TO A RELATED APPLICATION

The present application claims the benefit of U.S. Provisional Application Ser. No. 62/080,560, filed Nov. 17, 2014, which is incorporated by reference herein in its entirety, including any figures, tables, and drawings.

BACKGROUND OF INVENTION

Computed Tomography (CT) is a mainstay in diagnostic imaging. It plays key roles in disease detection and characterization, and also in patient follow-up during and after treatment. Biological soft tissue consists mainly of light elements, and its density is nearly uniform with little variation. Conventional attenuation-based X-ray imaging cannot provide sufficient contrast for biological soft tissue. X-ray phase imaging is sensitive to structural variation of soft tissue and offers superior contrast resolution for characterization of cancerous and other diseased tissues. The cross-section of an X-ray phase shift image is a thousand times greater than that of X-ray attenuation in soft tissue over the diagnostic energy range. This implies that phase imaging can achieve a much higher signal-to-noise ratio and substantially lower radiation dose than attenuation-based X-ray imaging.

Grating interferometry is a state of the art X-ray imaging approach, which can simultaneously acquire information of X-ray phase-contrast, dark-field, and linear attenuation. Conventional grating interferometers often use flat gratings, with serious limitations in the field of view and the flux of photons.

BRIEF SUMMARY

The subject invention provides novel and advantageous systems and methods for X-ray phase-contrast imaging (PCI), including the use of one or more period-varying or quasi-periodic gratings. An X-ray PCI system can include a phase grating that is period-varying or quasi-periodic and can be positioned between an object being imaged and a detector. A second grating, such as an absorption grating or an analyzer grating can also be present and disposed between the phase grating and the detector. One or both of the gratings (phase grating and absorption or analyzer grating) can be curved, such as a cylindrical (e.g., curved like a portion of a cylinder) or spherical (e.g., curved like a portion of a sphere) grating. Alternatively, one or both of the gratings (phase grating and absorption or analyzer grating) can be flat. The detector array can be curved or flat. For example, the detector can be a flat detector array.

The subject invention also provides second-order approximation models for X-ray phase retrieval, for example using paraxial Fresnel-Kirchhoff diffraction theory. An iterative method can be used to reconstruct a phase-contrast image and/or a dark-field image. The models can be iteratively solved using the algebraic reconstruction technique (ART). State of the art compressive sensing techniques can be incorporated to achieve high quality image reconstruction.

In an embodiment, an X-ray PCI system can include an X-ray source, a detector, a first grating disposed between the energy source and the detector, and a second grating disposed between the first grating and the detector, wherein the first grating is a quasi-periodical phase grating such that the period of the grating varies across the grating.

In another embodiment, a method of performing X-ray PCI can include providing an X-ray PCI system as described herein, positioning an object to be imaged between the X-ray source and the first grating, and imaging the object using the system.

In another embodiment, a method of reconstructing or retrieving an X-ray phase image can include approximating the image with a second-order approximation model using paraxial Fresnel-Kirchhoff diffraction theory.

BRIEF DESCRIPTION OF THE DRAWINGS

FIG. 1A shows a schematic of a curved-detector-based X-ray imaging system.

FIG. 1B shows a schematic of a flat-detector-based X-ray imaging system.

FIG. 9A shows a schematic of an X-ray imaging system with spherical gratings according to an embodiment of the subject invention.

FIG. 9B shows a spherical grating for 1D grating.

FIG. 9C shows a spherical grating for 2D grating.

FIG. 10A shows a setup of a grating-based PCI system.

FIG. 10B shows a setup of a grating-based PCI system.

FIG. 13A shows a schematic view of an experimental setup.

FIG. 13B shows images of interference fringes at 0° on the observation plane.

FIG. 13C shows images of interference fringes at 7.4° on the observation plane.

FIG. 13D shows images of interference fringes at 12.24° on the observation plane.

DETAILED DISCLOSURE

The subject invention provides novel and advantageous systems and methods for X-ray phase-contrast imaging (PCI), including the use of one or more period-varying or quasi-periodic gratings. An X-ray PCI system can include a phase grating that is period-varying or quasi-periodic and can be positioned between an object being imaged and a detector. A second grating, such as an absorption grating or an analyzer grating can also be present and disposed between the phase grating and the detector. One or both of the gratings (phase grating and absorption or analyzer grating) can be curved, such as a cylindrical (e.g., curved like a portion of a cylinder) or spherical (e.g., curved like a portion of a sphere) grating. Alternatively, one or both of the gratings (phase grating and absorption or analyzer grating) can be flat. The detector array can be curved or flat. For example, the detector can be a flat detector array.

In an embodiment, a system for imaging (e.g., X-ray imaging such as X-ray PCI) can include an energy source (e.g., an X-ray source), a detector, a first grating that is a period-varying or quasi-periodical phase grating positioned between the energy source and the detector, and a second grating positioned between the first grating and the detector. The second grating can be an absorption grating or an analyzer grating. Each of the first and second gratings can be curved, such as a cylindrical (e.g., curved like a portion of a cylinder) or spherical (e.g., curved like a portion of a sphere) grating or flat. The object to be imaged would be positioned between the energy source and the first grating. The system can optionally include a source grating positioned near the energy source, wherein the object to be imaged would be positioned between the source grating and the first grating. The source grating can be curved, such as a cylindrical (e.g., curved like a portion of a cylinder) or spherical (e.g., curved like a portion of a sphere) grating or flat.

In an embodiment, the detector is a flat detector, such as a flat detector array. The first grating can be curved, such as a cylindrical or spherical grating. The second grating can be flat to match the curvature (or lack thereof) of the detector. The optional source grating, if present, is curved, such as a cylindrical or spherical grating.

Figure 3A:
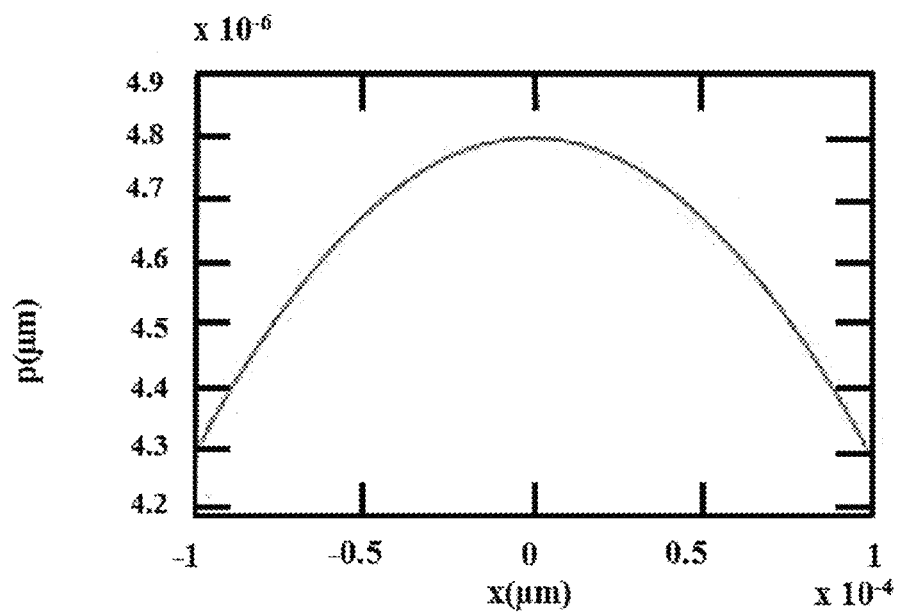
FIG. 3A shows a plot of period along the x-axis for a period-varying phase grating according to an embodiment of the subject invention.

The period-varying or quasi-periodical grating (e.g., period-varying or quasi-periodical phase grating) can have a predetermined or set period at the lateral point where the energy source is centered on the grating. The period can then change as the position on the grating is moved outwardly away along the surface of grating. In an embodiment, the period can change equally in both directions, such that the period at a given angle from the center point is the same as the negative of that given angle from the center point (e.g., as shown in FIGS. 3A and 11C).

Embodiments of the subject invention also provide spherical and/or cylindrical grating interferometers, and Talbot self-imaging with gratings of a slow-varying-period. Image quality can be improved and field of view (FOV) can be enlarged.

Imaging systems of the subject invention allow perpendicular incidence of X-rays on one or more of the gratings, giving higher photon flux and visibility, and a larger FOV. Imaging can be performed on larger sized objects than with a conventional interferometer with flat gratings. Imaging systems and methods of the subject invention have great utility for many preclinical and clinical applications.

The subject invention also provides second-order approximation models for X-ray phase retrieval, for example using paraxial Fresnel-Kirchhoff diffraction theory. An iterative method can be used to reconstruct a phase-contrast image and/or a dark-field image. The models can be iteratively solved using the algebraic reconstruction technique (ART). State of the art compressive sensing techniques can be incorporated to achieve high quality image reconstruction. In an embodiment, an iterative method can be used for phase reconstruction (e.g., based on Equation (42) below), and the method can include Equation (46) below. Equation (46) can be discretized to a system of linear equations with respect to variables $p_k(r)$. Then, the ART can be employed for phase image reconstruction.

The second-order phase approximation models for X-ray phase retrieval, and iterative algorithms, can be used for both in-line phase-contrast and dark-field imaging. These models accurately establish quantitative correspondence between phase shifts and image intensities, outperforming the related art linear phase approximation model used for X-ray in-line phase contrast imaging, because the linear model assumes slow phase variation and weak linear attenuation of an object.

The second-order approximation models disclosed herein can accurately establish a quantitative correspondence between phases and recorded intensity images, outperforming the related art linear phase approximation models used in the conventional methods of X-ray in-line PCI.

X-ray PCI is fundamentally different from conventional X-ray imaging and exhibits superior contrast resolution in various basic and applied areas. PCI relies on phase-shifts of X-ray waves, instead of their amplitude changes. In principle, the X-ray PCI is much more sensitive than attenuation-based imaging in the cases of weak-absorption materials. PCI can be used in many areas, including clinical applications. Three main types of X-ray phase retrieval for PCI are the propagation-based method, the analyzer-based method, and the grating-based method. Among these, the grating-based method has particularly good cost-effectiveness and established performance. Grating-based PCI has been used extensively in, for example, studying breast tissues and joint structures, and even with prototype machines.

The grating-based PCI method has been implemented with synchrotron radiation and has been extended to work under laboratory conditions by adding a third grating in certain situations. Grating-based PCI is based on the Talbot self-imaging principle, and it utilizes a near-field diffraction effect. That is, when coherent light passes through a periodic grating, the wave pattern right after the grating repeats itself at multiple distances. Based on the Talbot effect, phase shifts of incident X-ray waves induced by an object in the wave field can be extracted by comparing the grating self-imaging patterns with and without the object. The phase-stepping method is often used for data collection in such a grating interferometer.

Grating-based PCI can also be used for small field-of-view (FOV) imaging. However, it can sometimes be difficult to increase the FOV with conventional systems, due to several issues related to not only grating fabrication but also physical modeling. Theoretically speaking, the beam divergence cannot be neglected in the case of a large beam angle for which the paraxial approximation is no longer valid. The subject invention addresses this problem by utilizing the Talbot self-imaging method with one or more quasi-periodic gratings. This is effective for many applications, including performing user-defined self-imaging and being part of an optimal system design for grating-based PCI with a large FOV.

X-ray imaging machines are widely used in pre-clinical and clinical examinations. Such machines use X-ray tubes and X-ray detectors, integrated with electrical and mechanical parts. According to the detector type, they can be classified into flat- and curved-detector systems. FIG. 1A shows a schematic of a curved-detector-based X-ray imaging system, and FIG. 1B shows a schematic of a flat-detector-based X-ray imaging system. Much of the derivation presented herein focuses on fan-beam imaging geometry (FIG. 1A) and not the cone-beam counterpart (FIG. 1B), but the fan-beam principles can be extended to the cone-beam case. The imaging plane can be considered where X-rays stay, and are characterized by an angle $\lambda$ with respect to a central line on the imaging plane. In the curved-detector system, as shown in FIG. 1A, the distance between an X-ray source and each detector cell is a constant, $D=D_0$. In the flat-detector system, as shown in FIG. 1B, the distance is described as a parabolic function $$D_i = \sqrt{D_0^2 + (i\Delta_x)^2}, \quad (1)$$

where $i=0, \pm 1, \pm 2, \ldots$, indexing the positions of detector cells, and $\Delta x$ is the cell pitch. Approximated by the Taylor series, Equation (1) can be written as $$D_i \approx D_0 + \frac{1}{2D_0}(i\Delta_x)^2. \quad (2)$$

The Talbot self-imaging phenomenon is understood in the art. Let a periodic grating be infinite long along the x-axis:

$$t(x) = \sum_{i=-\infty}^{+\infty} g(x - ip) = g(x) \otimes \sum_{i=-\infty}^{+\infty} \delta(x - ip) \quad (3)$$

where $i=0, \pm 1, \pm 2, \ldots$, $\otimes$ is a convolution operator, p is the grating period, and g(x) gives the complex amplitude at individual grating apertures.

If the case of a fully coherent parallel beam with a wavelength $\lambda$ is considered, the wave field, $w_t(x)$, right after the grating, is described by t(x) (Equation (3)). Then, the Fourier transform of $w_t(x)$ is $$W(k_x) = FT\{w_t(x)\} = FT\{t(x)\} \propto \sum_{j=-\infty}^{+\infty} G(k_x) \cdot \delta(k_x - jK_0) = \sum_{j=-\infty}^{+\infty} G(jK_0) \quad (4)$$

in which FT denotes the Fourier transform, $j=0, \pm 1, \pm 2, \ldots$, $G(k_x)=FT\{g(x)\}$, and $$K_0 = \frac{2\pi}{p}.$$

With the X-ray propagation after the grating, the diffraction phenomenon is expressed as by the Fresnel approximation $$w_{t,d}(x) = w_t(x) \otimes F_d(x) \quad (5)$$

in which d specifies the propagation distance, and F(x) is the Fresnel operator defined by $$F_d(x) = \frac{\exp\left(i\frac{2\pi}{\lambda}d\right)}{i\lambda d}\exp\left(i\frac{\pi}{\lambda d}x^2\right) \quad (6)$$

The Fourier transform of Equation (5) can be found to be $$W_d(k_x) = FT\{w_{t,d}(x)\} \propto \exp\left(i\frac{\lambda d}{4\pi}k_x^2\right)\sum_{j=-\infty}^{+\infty} G(jK_0) \approx \quad (7)$$

$$\sum_{j=-\infty}^{+\infty} \exp\left(i\frac{\lambda d}{4\pi}(jK_0)^2\right)G(jK_0) = \sum_{j=-\infty}^{+\infty} \exp\left(i\frac{\lambda d\pi}{p^2}j^2\right)G(jK_0)$$

According to Equation (7), when $$d = d_T = 2n\frac{p^2}{\lambda},$$

where $n=1, 2, 3, \ldots$, a similar wave front is formed, and $d_T$ is called the Talbot distance. Further, the same intensity pattern can be repeated at the distance $$d = m\frac{p^2}{8\lambda},$$

where m is an odd integer.

In the case of fan-beam illumination, as shown in FIG. 1B, the wave front at the grating position is w, and its wave phase is distributed as a quadratic function $$w(x) = \exp\left(i\alpha \frac{2\pi}{\lambda} x^2\right),$$

in which α defines the curvature of the quadratic phase profile, determined by the distance between the X-ray source and the grating position D, $$\alpha = \frac{1}{2D},$$

as derived from Equations (1) and (2).

Thus, the wave complex amplitude $w_t(x)$ immediately after the phase grating is $$w_t^{fan}(x) = w(x) \cdot t(x) = w(x) \sum_{i=-\infty}^{+\infty} g(x-ip) \approx \sum_{i=-\infty}^{+\infty} w(ip)g(x-ip) \quad (8)$$

According to Equation (5), the Fourier transform of the wave front after a short propagation distance d is $$\begin{aligned} w_d^{fan}(k_x) &= FT\{w_{t,d}^{fan}(x)\} \quad (9)\\ &\propto \sum_{j=-\infty}^{+\infty} \exp\left(i\frac{\lambda d\pi}{p^2} j^2\right)\exp\left(i\frac{\lambda D\pi}{p^2} j^2\right)G(jK_0)\\ &= \sum_{j=-\infty}^{+\infty} \exp\left(i\frac{\lambda(d+D)\pi}{p^2} j^2\right)G(jK_0) \end{aligned}$$

With the magnification effect of fan-beam geometry, the fractional Talbot distance is $$d = m\frac{p^2}{8\lambda}\frac{D+d}{D} \quad (10)$$

which is the counter part of the Talbot lengths in the parallel-beam case, with the magnification factor (D+d)/D.

Figure 2A:
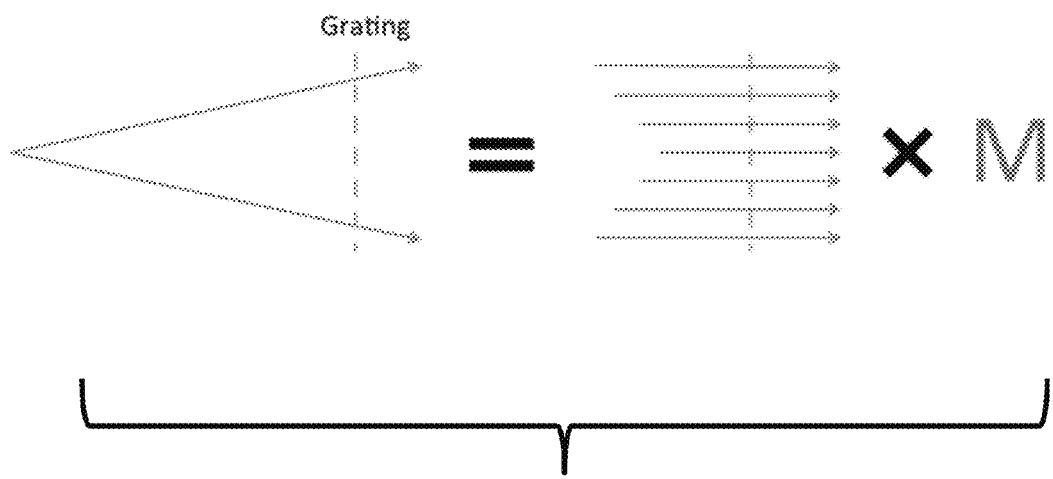
FIG. 2A shows a representation of flat-grating-based fan-beam Talbot self-imaging.
Figure 2B:
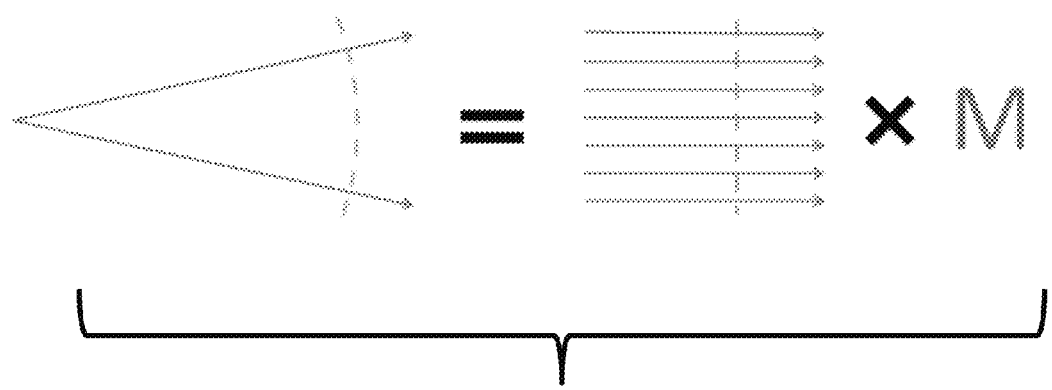
FIG. 2B shows a representation of curved-grating-based fan-beam Talbot self-imaging.

FIG. 2A shows a representation of flat-grating-based fan-beam Talbot self-imaging. FIG. 2B shows a representation of curved-grating-based fan-beam Talbot self-imaging. Talbot self-imaging is equivalent to parallel-beam imaging with an appropriate phase initialization. The magnification factor (M) due to fan-beam geometry should be considered.

Comparing Equations (7) and (9), it is clear that the behavior of fan-beam Talbot self-imaging is similar to that of the parallel-beam case, except that there is a quadratically-distributed initial phase at the grating position in the fan-beam case. Hence, as shown in FIG. 2A, flat-grating-based fan-beam Talbot imaging is equivalent to the parallel-beam situation by setting the initial phase distribution and taking the fan-beam magnification. In addition, with curved-grating-based fan-beam Talbot imaging, the distance between the X-ray source and each grating aperture is constant, and only the system magnification is needed, as shown in FIG. 2B.

The Talbot effect is based on periodic gratings, which repeats the same intensity pattern at different distances after the grating. Embodiments of the subject invention can utilize Talbot self-imaging with quasi-periodic period gratings. This can result in more freedom in designing the intensity profile for phase-contrast imaging.

A quasi-periodic grating can be defined as $$t'(x) = \sum_{i=-\infty}^{+\infty} g_{p'(i)}(x-X(i)) \quad (11)$$

where X(i) denotes the grating aperture position along the x-axis, indexed by i, and p'(i) is the width of the corresponding grating aperture. A grating with a slow-varying period can be approximated by a composition of periodic gratings, written as $$\begin{aligned} t'(x) &\approx \frac{1}{2N}\sum_{i=-\infty}^{+\infty}\sum_{i_L=i-N}^{i+N} g_{p'(i)}(x-X(i)) \quad (12)\\ &= \frac{1}{2N}\sum_{i=-\infty}^{+\infty}\left(g_{p'(i)}(x) \otimes \sum_{p_L=-N}^{+N} \delta(x-X(i)-i_Lp'(i))\right)\\ &= \frac{1}{2N}\sum_{i=-\infty}^{+\infty}\left(g_{p'(i)}(x) \otimes \left(t_{trunc}(i,2N)\sum_{i_L=-\infty}^{+\infty} \delta(x-X(i)-i_Lp'(i))\right)\right) \end{aligned}$$

where $i_L$ defines a local grating aperture location corresponding to the index i, and $t_{trunc}(i,2N)$ is a grating envelope associated with the finite grating length 2N, centered at the ith-indexed position. If each individual grating aperture is short enough relative to the grating truncation length 2N, Equation (12) can be further simplified to $$t'(x) \approx \frac{1}{2N}\sum_{i=-\infty}^{+\infty}\left(g_{p'(i)}(x) \otimes \sum_{i_L=-\infty}^{+\infty} \delta(x-X(i)-i_Lp'(i))\right) \quad (13)$$

The accuracy of the approximation in Equation (13) can be measured as $$\frac{|Np'(i)-(X(i)-X(i-N))|}{p'(i)} \quad (14)$$

that quantifies the maximum local linear representation error. The accuracy of this is discussed in Examples 1 and 2 based on a real imaging scenario, where the system size was much larger than the grating aperture width.

Comparing Equations (3) and (13), it is found that the period-varying grating is a set of super-positioned periodic gratings, and has the same Talbot self-imaging property as that of periodic gratings. Thus, the fractional Talbot length of the period-varying grating should resemble that of the conventional periodic gratings, but the Talbot length is changed along the x-axis and determined by corresponding grating aperture size p'(i) expressed as $$d = m\frac{p'(i)}{8\lambda} \quad (15)$$

in the parallel-beam case and $$d = m\frac{D+d}{D}\frac{p'(i)}{8\lambda} \qquad (16)$$

in the fan-beam case. With Equation (15) or Equation (16), it is feasible to design the self-imaging patterns for various benefits. The length between the grating and its self-imaging pattern is determined by the grating aperture size p'(i).

Figure 4A:
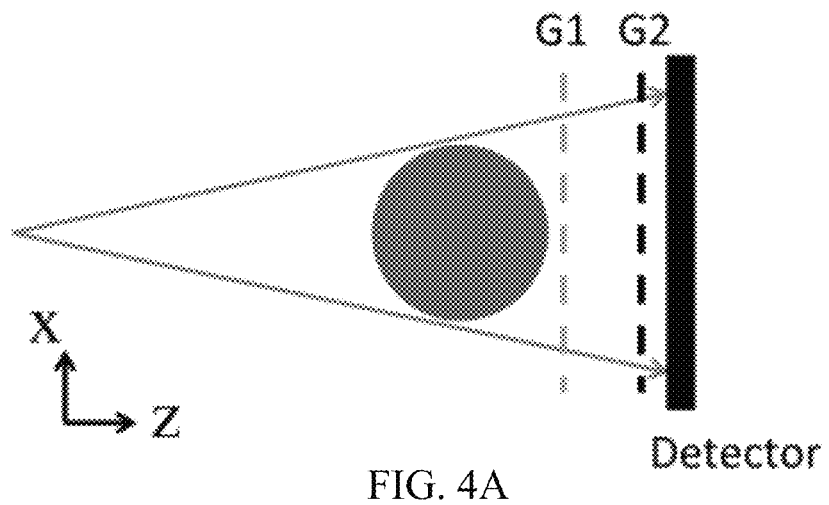
FIG. 4A shows a schematic view of a flat grating, flat detector system.
Figure 4B:
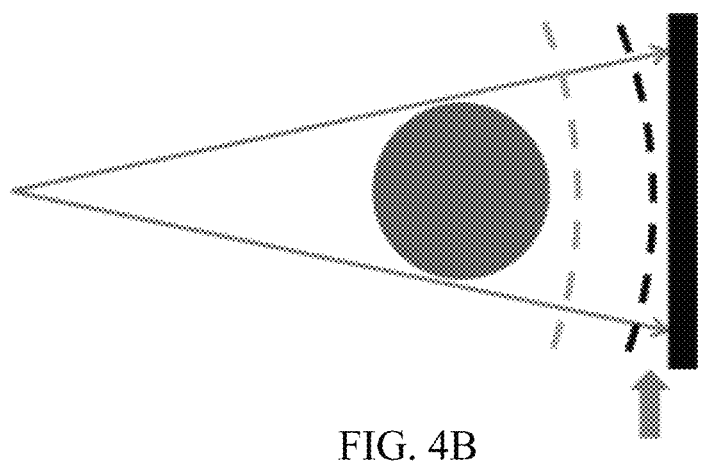
FIG. 4B shows a schematic view of a curved grating, flat detector system.
Figure 4C:
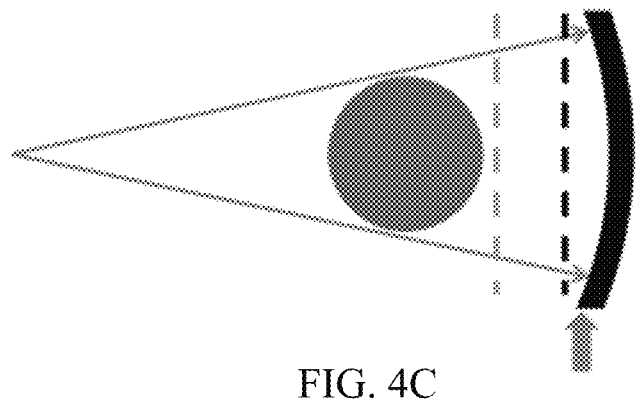
FIG. 4C shows a schematic view of a flat grating, curved detector system.
Figure 4D:
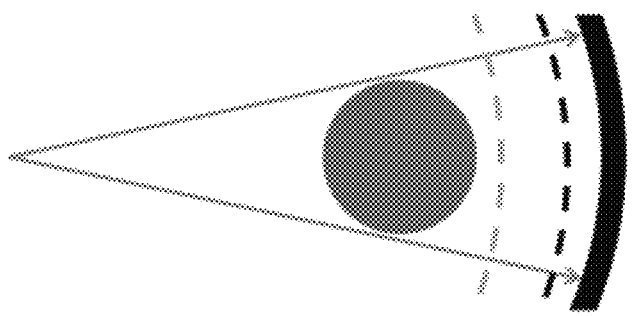
FIG. 4D shows a schematic view of a curved grating, curved detector system.

In a grating-based PCI system, a phase grating G1 and an absorption grating G2 can be placed between an object and a detector, as shown in FIGS. 4A-4D. Curved gratings can be used as well, as shown in FIG. 1B, to match the X-ray beam divergence. Similarly, in a curved-detector system (FIG. 1A), flat and curved grating sets can be installed for phase-contrast imaging. Thus, four kinds of grating-based PCI systems include: flat grating, flat detector; curved grating, flat detector; flat grating, curved detector; and curved grating, curved detector. FIG. 4A shows a schematic view of a flat grating, flat detector system. FIG. 4B shows a schematic view of a curved grating, flat detector system. The red arrow highlights the non-uniform gaps between the absorption grating G2 and the detector. FIG. 4C shows a schematic view of a flat grating, curved detector system. The red arrow highlights the non-uniform gaps between the absorption grating G2 and the detector. FIG. 4D shows a schematic view of a curved grating, curved detector system.

If the detector and the absorption grating G2 have different curvatures as indicated by the red arrows in FIGS. 4B and 4C, there are non-uniform gaps between the grating G2 and the detector. The non-uniform gap distribution can introduce non-uniform image artifacts due to the blurring effect from the X-ray spot. Therefore, the absorption grating G2 should be placed as closely as possible to the detector plane, for example as in FIGS. 4A and 4D.

Figure 5A:
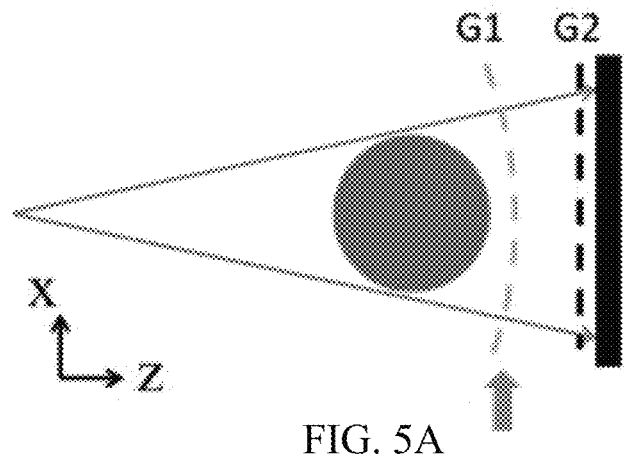
FIG. 5A shows a schematic view of a grating-based phase-contrast system.
Figure 5B:
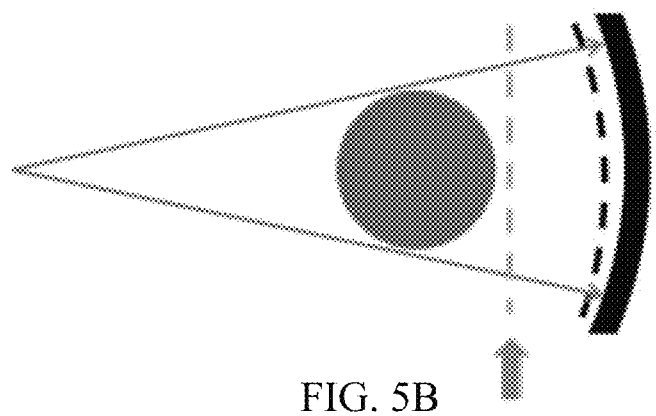
FIG. 5B shows a schematic view of a grating-based phase-contrast system.
Figure 5C:
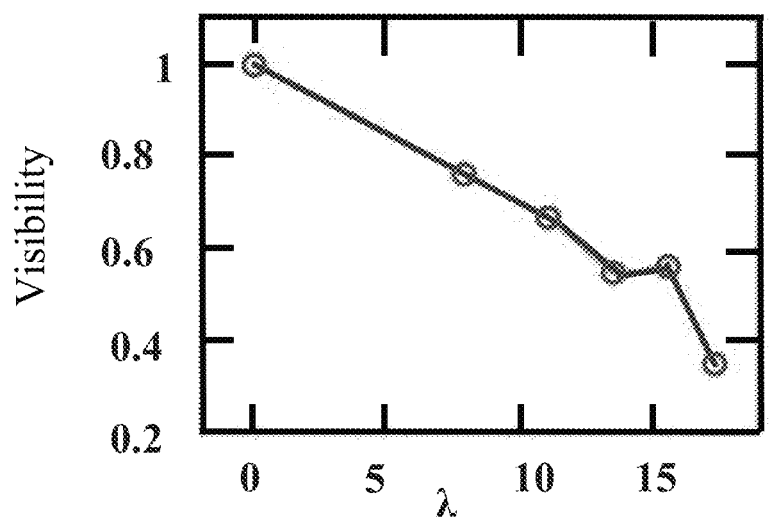
FIG. 5C shows a plot of the visibility versus angle for the setup of FIG. 5A.
Figure 5D:
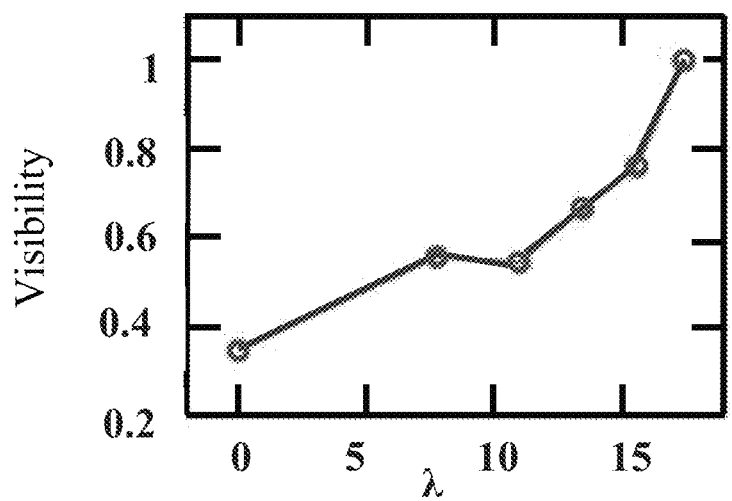
FIG. 5D shows a plot of the visibility versus angle for the setup of FIG. 5B.

The designs in FIGS. 4A and 4D can also have issues due to imperfect fabrication of the gratings and/or difficulty in matching the gratings to the beam divergence. This can lead to the phase grating G1 and absorption grating G2 not being exactly paired, as shown in FIGS. 5A and 5B. FIG. 5A shows a schematic view of a grating-based phase-contrast system with a curved G1 and a flat G2 (and flat detector), and FIG. 5B shows a schematic view of a grating-based phase-contrast system with a flat G1 and a curved G2 (and curved detector). FIG. 5C shows a plot of the visibility versus angle (in degrees) for the setup of FIG. 5A, and FIG. 5D shows a plot of the visibility versus angle (in degrees) for the setup of FIG. 5B.

Figure 6A:
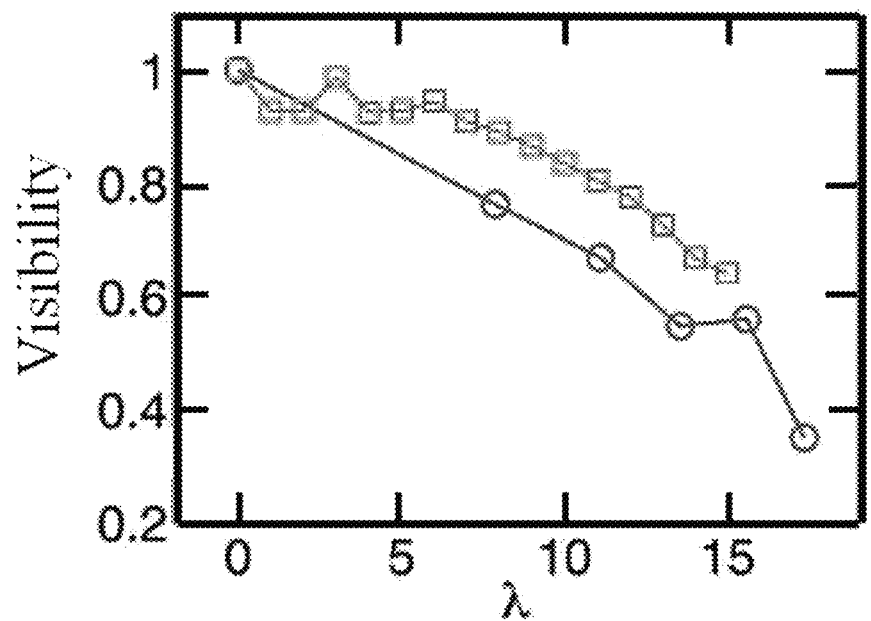
FIG. 6A shows a plot of visibility versus angle.
Figure 6B:
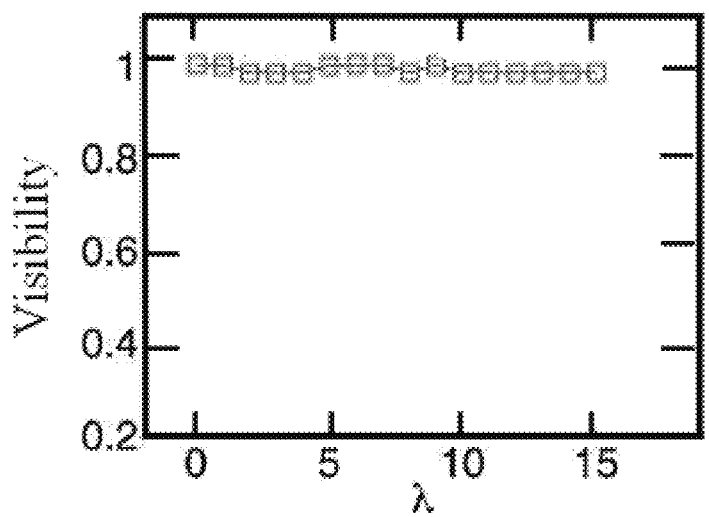
FIG. 6B shows a plot of visibility versus angle.

FIG. 6A shows a plot of visibility versus angle (in degrees) for the unpaired G1-G2 system of FIG. 5A and a period-unmatched imaging system. The red line (upper line) is for the period-unmatched system, and the blue line (lower line) is for the system of FIG. 5A). FIG. 6B shows a plot of visibility versus angle (in degrees) for a period-matched imaging system. In a grating-based PCI system, a periodic phase grating can be adopted to produce the same interference patterns at a Talbot length. However, if the phase grating and absorption grating are not paired (as in FIGS. 5A and 5B), the absorption grating may not be located exactly on the interference patterns. The visibility of the stepping curve can then be degraded. FIGS. 5C and 5D show results with respect to the angle in the fan beam.

In many embodiments of the subject invention, a phase grating can be a period-varying grating, and can be paired with, e.g., a flat absorption grating G2 (FIG. 5A) or a curved absorption grating G2 (FIG. 5B). The phase gratings shown in FIGS. 5A and 5B can be designed using Equation (16).

The results are shown in FIG. 6A, compared with the unpaired G1-G2 system of FIG. 5A. To match the period-varying G1, the grating G2 can be accordingly modified by $$p'_{G2}(i) = \frac{p'_{G1}(i)}{2}\frac{D+d}{D}. \qquad (17)$$

FIG. 6B shows that the period-matched G1 and G2 is an optimized grating-based PCI system with a nearly-uniform visibility distribution within the fan beam range.

In the related art, high-energy and large FOV PCI imaging is a major technical challenge. In the case of a large FOV, as the fan beam angle increases, the X-ray beam divergence becomes significant enough to degrade the imaging performance. A curved grating structure can thus be used in embodiments of the subject invention. Flat-panel detectors are widely used in practice due to low cost and high spatial resolution. This requires a flat absorption grating G2 to match the detector shape, avoiding the non-uniform gap between the detector and G2. This can lead to a curved phase gating G1 and flat absorption grating G2 being unpaired, as shown in FIG. 5A. Similar issues exist for a curved-detector imaging system, as shown in FIG. 5B. To solve this problem, embodiments of the subject invention advantageously use one or more period-varying gratings (e.g., a Talbot self-imaging method with a period-varying grating). By modifying the individual grating aperture width, the Talbot self-imaging lengths can be determined to match the spatial non-uniformity between G1 and G2, allowing the G2 to be placed exactly (or nearly exactly) on the self-imaging pattern of G1.

The performance of a grating design of the subject invention can be quantified, for example, by the maximum local linear representation error defined by Equation (14). To make the error less than 5%, in an imaging system used in practice (e.g., a 4.8 μm G1 period and 1 m source-to-G1 distance), the value of N in Equation (14) should be about $1 \times 10^4$, which is large enough to satisfy the approximation in Equation (13). The grating length truncation will not influence the beam decomposition and reformation (see also, e.g., FIGS. 2A and 2B).

Period-varying gratings of the subject invention generate uniform visibility distribution within the fan beam range, leading to excellent imaging performance. Thus, Talbot self-imaging methods with period-varying grating(s) can facilitate system design and improve imaging performance. The phase grating G1 can be curved to match the divergence of an X-ray fan-beam, and the absorption grating G2 can be adapted to match a flat detector (e.g., FIGS. 4D and 5A). This can lead to large FOV clinically-oriented imaging systems.

X-ray PCI based on grating interferometry has exhibited superior contrast in biological soft tissue imaging. The high sensitivity relies on the high-aspect ratio structures of the planar gratings, which prohibit the large field of view applications with a diverging X-ray source. Curved gratings allow a high X-ray flux for a wider angular range, but the interference fringes are only visible within ~10° range due to the geometrical mismatch with the commonly-used flat array detectors. Embodiments of the subject invention use a curved quasi-periodic grating for large FOV imaging, even with a flat detector array. This can lead to, for example, an interference fringe pattern with less than a 10% decrease in visibility over 25°.

X-ray PCI can detect small variations of the refractive index, providing superior contrast for low-elements compared with attenuation contrast, and thus is advantageous in imaging biological soft tissues, such as vessels, lesions, and micro-calcifications.

FIGS. 10A and 10B show setups of grating-based PCI systems. FIG. 10A shows two flat gratings G1 and G2, and FIG. 10B shows a curved phase grating G1 and a flat analyzer grating G2. A flat panel detector can be placed immediately after G2. In the case of using an X-ray tube with low spatial coherence, another grating G0 (omitted in FIGS. 10A and 10B; see also FIG. 9A) can be used between the source and the object.

During the imaging process, phase stepping of the analyzer grating G2 can be induced, and the information of X-ray attenuation, phase contrast, and small angle scattering can be acquired simultaneously. The PCI sensitivity relies on the frequency of the interference fringes. Flat gratings with high aspect ratio structures are ideal for parallel beams. However, in most non-synchrotron setups, the divergent radiation emerges from the focus of the X-ray tube; therefore, the FOV in the X-ray interferometer is limited to only a few centimeters. The use of a curved phase grating G1 allows perpendicular incidence of X-rays on the gratings, permitting a high X-ray flux with a wider acceptance angle than that associated with a flat grating. In such a setup, a curved phase grating G1 can generate a self-image on a curved analyzer grating G2, posing a geometrical mismatch with a flat panel detector. This mismatch is position-dependent and grows nonlinearly as the angle (from straight ahead from the source onto the grating) increases. As a result, the mismatch can cause a reduction of the visibility of the stepping curve at larger angles and limit the FOV of the curved grating setups. The stepping visibility is defined as the ratio between the amplitude and the mean of the phase stepping curve.

FIG. 9A shows a schematic of an X-ray imaging system with spherical gratings. The system can include an X-ray source, a spherical phase grating G1, and a spherical analyzer grating G2. The object to be imaged can be positioned between the source and the phase grating G1. An optional spherical source grating G0 is also shown in FIG. 9A. FIG. 9B shows a spherical grating for 1D grating. FIG. 9C shows a spherical grating for 2D grating. The use of spherical gratings (e.g., with a common X-ray tube as a point source) can allow perpendicular incidence of X-rays on the gratings, thereby resulting in higher flux and higher visibility, and a larger field of view than a conventional interferometer with flat gratings. The source grating G0, if present, can be placed close to the source to form an aperture mask with transmission elements and can generate an array of periodically repeating sources. The phase grating G1 can act as a phase mask for the phase modulations onto the incoming wave field. Through the Talbot effect, the phase modulation can be transformed into an intensity modulation in the plane of the analyzer grating G2 to form a periodic fringe pattern. The third (analyzer) grating G2 can have the same period and orientation as the fringes created by G1 to extract X-ray phase variation induced by the object being imaged.

In many embodiments, a curved quasi-periodic phase grating G1' can be used in a PCI system or method. The grating can have a self-image that occurs on a flat plane, thereby advantageously allowing the use of a flat analyzer (or absorption grating) G2 to match the detector (i.e., flat detector) to eliminate the geometric mismatch for a larger FOW in PCI with a flat panel detector, as shown in FIG. 10B.

The self-imaging effect of an infinite periodic planar structure can be formulated by geometrical ray tracing and scalar diffraction theory under paraxial approximation. An angular decomposition approach can be used to derive the Talbot distance for one dimensional (1D) curved gratings in polar coordinates. The analysis presented herein is not limited to binary transmission gratings, but also applicable to phase gratings, which are more common as gratings G1 in X-ray PCI setups.

In diffraction theory, the vector field can be treated as a scalar field under two conditions: 1) the feature size of the object along the polarization direction of the field is much larger than the wavelength; 2) all components of vector field obey the same scalar wave equation. In general, the second condition is not satisfied in cylindrical coordinates. Scalar diffraction theory is applicable, though, for the grating analysis for the X-ray PCI imaging. Assuming $r_0 \gg p \gg \lambda$, the electric field components in free space diffracted by the grating G1 can be expressed as a sum of its Fourier series:

$$E_z = \sum_{m \in Z} a_m H_m^{(2)}(kr) \cdot e^{im\theta}, \tag{18}$$

$$E_\theta = \frac{i\eta_0}{k} \sum_{m \in Z} b_m \frac{\partial}{\partial r} H_m^{(2)}(kr) e^{im\theta}, \tag{19}$$

$$E_r = \frac{\eta_0 m}{kr} \sum_{m \in Z} b_m H_m^{(2)}(kr) e^{im\theta}, \tag{20}$$

where $\eta_0 = 1/(\epsilon_0 c)$, is the impedance of the free space, $k = 2\pi/\lambda$, is the wavenumber, $r > r_0$, $H_m^{(2)}(kr)$ is Hankel function of the second kind representing the outgoing wave, and m is an integer. For a curved grating with period p, m is given by $2n\pi r_0/p$, where n is an integer. In the case of an X-ray PCI setup, $r_0 \gg p \gg \lambda$. Thus, the asymptotic expansions of modulus and the phase of $H_m^{(2)}(kr)$ can be used:

$$|H_m^{(2)}(kr)| = \sqrt{\frac{2}{\pi kr} + \frac{4m^2 - 1}{2 \cdot (2kr)^2} + \dots}, \tag{21}$$

$$\arg H_m^{(2)}(kr) = -kr + \left(\frac{1}{2}m + \frac{1}{4}\right)\pi - \frac{4m^2 - 1}{8kr} + \frac{(4m^2 - 1)(4m^2 - 9)}{6 \cdot (4kr)^3} + \dots, \tag{22}$$

These asymptotic expansions are valid for kr much greater than m, i.e., m/kr≪1. Substituting Equation (21) and Equation (22) into Equation (18), (19), and (20) yields the approximated expressions of the outwardly propagating electric field. Under the condition $r_0 \gg p \gg \lambda$, further approximation can be made as $H'm^{(2)}/k \approx -i\, Hm^{(2)}$. The three components of the electric field reduce to $$E_z = \sum_{m \in Z} a_m H_m^{(2)}(kr) \cdot e^{im\theta}, \tag{23}$$

$$E_\theta = \eta_0 \sum_{m \in Z} b_m H_m^{(2)}(kr) \cdot e^{im\theta}, \tag{24}$$

$$E_r = \frac{m}{kr} \eta_0 \sum_{m \in Z} b_m H_m^{(2)}(kr) \cdot e^{im\theta}, \tag{25}$$

where $r > r_0$, $H_m^{(2)}(kr)$ are approximated by Equation (21), and Equation (22) shows that $E_r$ decays faster along the direction of r than the other two components. Because $m/kr \ll 1$, $E_r \ll E_0$. The component $E_r$ can be ignored. The other two components of the electric fields have the same form. The components of the magnetic field have similar results. Therefore, under the condition $r_0 \ll p \ll \lambda$, all the field components have the same form, and the polarization of the electric field is perpendicular to the r direction. Because the two conditions for using scalar diffraction theory are both satisfied, one scalar field $u(\theta, r_0)$ can be used to represent any field component in cylindrical coordinates, $$u(\theta, r) = \sum_{m \in Z} c_m \cdot \frac{1}{\sqrt{kr}} e^{-kr + \frac{m}{2}\frac{4m^2-1}{8kr}} \cdot e^{im\theta}, \quad (26)$$

where $c_m$ is the complex Fourier coefficient.

Referring to FIG. 10B, a curved grating G1, whose center is located at the origin of the coordinate system, can have a radius of $r_0$. The point source can also be placed at the origin. The angular span of the grating can be assumed to be small in the vertical direction, so the irradiance is uniform along the z-axis. In the case of an X-ray PCI setup, the radius of grating G1 (~1 m) is much greater than the period of G1 (~1 µm), and the period of G1 is much greater than the wavelength (~0.1 nm), i.e., $r_0 \gg p \gg \lambda$. Under these conditions, a scalar field, $u(\theta, r)$ representing the field after the grating G1 in cylindrical coordinates can be expressed by the sum of the angular Fourier series.

$$u(\theta, r) = \sum_{m=-\infty}^{\infty} c_m H_m^{(2)}(kr) \cdot e^{im\theta}, \quad (27)$$

where $r > r0$, m is an integer representing the angular frequency, $k = 2\pi/\lambda$, is the wave number, $H_m^{(2)}(kr)$ is the Hankel function of second kind representing the outgoing wave, and cm is the complex coefficient. For $kr \gg m$, the modulus and the phase of $H_m^{(2)}(kr)$ can be expressed asymptotically as:

$$|H_m^{(2)}(kr)| = \sqrt{\frac{2}{\pi kr} + O\left(\frac{1}{(kr)^2}\right)}, \quad (28)$$

$$\arg H_m^{(2)}(kr) = -kr\left(\frac{1}{2}m + \frac{1}{4}\right)\pi - \frac{4m^2-1}{8kr} + O\left(\frac{1}{(kr)^3}\right). \quad (29)$$

The scalar field at the boundary, $r = r_0$, can be considered, and the periodic scalar field can be also be expressed as the sum of its angular Fourier harmonics, $$u(\theta, r_0) = \sum_{m \in Z} A_m \cdot e^{im\theta}, \quad (30)$$

where $A_m$ denotes the angular Fourier coefficients. Matching the angular Fourier components of Equation (27) with Equation (30) and plugging in the asymptotic expansions in Equation (28) and Equation (29), $$u(\theta, r) = \sqrt{\frac{r_0}{r}} e^{i\left(kr_0 - kr + \frac{1}{8kr}\frac{1}{8kr_0}\right)} \cdot \sum_{m=-\infty}^{\infty} \left\{ e^{i\left(\frac{m^2}{2k}\left(\frac{1}{r_0} - \frac{1}{r}\right)\right)} \right\} \cdot A_m \cdot e^{im\theta}. \quad (31)$$

Equation (31) shows that the amplitude of the field decays as $1/\sqrt{r}$. The common phase term outside of the summation operation can be neglected, because only the phase term, $\exp(im^2(1/r_0 - 1/r)/2k)$, affects the intensity of the field. In analogy to the infinite periodic planar grating, the case where the circumference of the circle is a multiple of the grating period can be considered, and this ratio, $2\pi r_0/p$, can be considered as the fundamental angular frequency. Under this condition, the angular Fourier frequency components contain the harmonics of the fundamental angular frequency only, i.e., $m = 2\pi n r_0/p$, where n is an integer. When the field at radius $r_D$, satisfies the equation $$\frac{1}{r_D} = \frac{1}{r_0} - l \cdot \frac{2p^2}{\lambda r_0^2}, l = 1, 2, 3 \ldots, \quad (32)$$

the phase term, $\exp(im^2(1/r_0 - 1/r)/2k)$, is equal to a multiple of $2\pi$ for all the angular frequency m, which means that the field $g(\theta, r_D)$ and $g(\theta, r_0)$ have the same intensity distribution along the θ direction. Equation (32) indicates three facts of the Talbot effect of a curved periodic grating. First, the self-image is a magnified curved periodic grating sharing the same origin with the original grating G1. Second, the Talbot distance, $r_D - r_0$, has a non-linear relation with $p^2/\lambda$, which is different from the case of planar periodic gratings. Third, there are only a limited number of the self-images, since l is bounded.

Thus, a curved periodic grating can generate a magnified self-imaging grating on a curved plane. In a particular setup, the analyzer grating G2 is designed so that its period and curvature matches the self-image of G1. However, array detectors with matching curvature can be difficult or impractical to fabricate. Using a planar analyzer (absorption) grating G2 and flat detector, as depicted in FIG. 10B, will inevitably result in a loss of the contrast of the stepping curves at large angles if the phase grating has a constant period.

In many embodiments of the subject invention, one or more quasi-periodic gratings can be used to improve the contrast of the stepping curve on a flat detector and provide one more degree of freedom in the design. Specifically, the periodicity of the curved grating can be perturbed with a slow-varying term to create a flat self-imaging plane. As shown in Equation (32), the Talbot distance depends on the grating period p. By changing the period along the direction of θ, a quasi-periodic grating can be designed with a flat self-image plane. The quasi-periodic grating with slow-varying period can be expressed as:

$$g(\theta, r_0) = \sum_{i \in Z} rect\left(\frac{2r_0}{p_i}\theta\right) * \delta(\theta - \theta_i), \quad (33)$$

where rect(•) denotes the rectangular function, * denotes the convolution operation, and δ(•) is the Dirac-delta function. The term $p_i$ denotes the period of the grating at angle $\theta_i$, indexed by i. In a strictly periodic grating, $p_i$ is a constant, and $\theta_i = ip_i/r_0$. In a quasi-periodic grating, the angle $\theta_i$ holds the relation with $p_i$, $$\theta_i = \frac{1}{r_0}\left(\frac{p_0 + p_i}{2} + \sum_{j=1}^{|i-1|} p_j\right), i = 1, 2, 3 \ldots, \quad (34)$$

where $p_0$ denotes the central period of the quasi-periodic grating G1' at $\theta=0$. The quasiperiodic grating can be treated as a locally periodic grating for self-imaging, when 1) the amplitude of high harmonic diffraction order is small, $p_i \gg \lambda$, which is satisfied in X-ray PCI setups, and 2) the period of the quasi-periodic grating varies slowly. To design a flat self-image plane, the period of the quasi-periodic grating, $p_i$, satisfies the following equation:

$$\frac{2p_i^2}{\lambda r_0^2} + \frac{1}{r_0} = \left(\frac{2p_0^2}{\lambda r_0^2} + \frac{1}{r_0}\right) \cdot \cos(\theta_i), \quad (35)$$

Using Equation (34) and Equation (35), the period of the quasi-periodic grating G1' can be calculated at each angle iteratively.

In many embodiments, a curved quasi-periodic grating can be used for a large FOV X-ray PCI, even with a flat array detector. In comparison with using a periodic phase grating G1, a quasi-periodic grating can generate a Talbot self-imaging effect on a flat plane, and can thus increase the visibility over a larger range of view angle. Examples 3-5 demonstrate that the decrease of the fringe visibility is less than 10% within the view angle of 25°.

X-ray phase imaging is sensitive to structural variation of soft tissue, and offers excellent contrast resolution for characterization of cancerous tissues. Also, the cross-section of an X-ray phase shift is a thousand times greater than that of X-ray attenuation in soft tissue over the diagnostic energy range, allowing a much higher signal-to-noise ratio at a substantially lower radiation dose than attenuation-based X-ray imaging.

In an embodiment of the subject invention, a second-order approximation model can be used to reconstruct an X-ray image. The model can be with respect to phase shift based on the paraxial Fresnel-Kirchhoff diffraction theory. In-line dark-field imaging can also be performed based on the second-order model. The model can accurately establish a quantitative correspondence between phases and recorded intensity images, outperforming related art linear phase approximation models that are used in conventional methods of X-ray in-line phase-contrast imaging. In a further embodiment, the models of the subject invention can be iteratively solved using the algebraic reconstruction technique (ART). The state of the art compressive sensing techniques can be incorporated to achieve high quality image reconstruction. Numerical simulation studies presented in Examples 6 and 7 demonstrate the feasibility of the models that are more accurate and stable, and more robust against noise, than related art methods.

Biological soft tissues consist mainly of light elements with low atomic numbers, and the elemental composition is nearly uniform with little density variation. Hence, the X-ray attenuation contrast cannot yield sufficient sensitivity and specificity in many biomedical scenarios. On the other hand, the cross-section of X-ray phase shift is three orders of magnitude larger than that of X-ray attenuation in soft tissues over the diagnostic energy range. Hence, X-ray PCI is also advantageous to reveal subtle features of soft tissues and offer superior contrast for analyses of various normal and diseased conditions at a reduced radiation dose.

When a spatial coherent X-ray wave passes through an object, the X-ray wavefront is deformed by variation of the refractive index in an object. After coherent X-rays propagate a sufficient distance in a free space, a phase contrast is formed. In-line X-ray PCI can reconstruct phase shifts from image intensity measurements. This scheme offers unique merits in terms of simplicity and implementation. A relationship exists between the Fourier transform of a Fresnel diffraction pattern and the autocorrelation of a transmittance function, and a contrast transfer function (CTF) method can be used to reconstruct phase shifts based on an assumption of weak absorption and slow phase change. Paraxial Fresnel-Kirchhoff diffraction theory can be applied to establish a transport of intensity equation (TIE) to describe a relationship between intensity data and phase shifts. With intensity measurements at several distances along its propagation direction, the phase information can be quantitatively retrieved. An auxiliary function can transform TIE into a classical two-dimensional Poisson equation, which can be solved using a Fourier transform method, or a Green function method with suitable boundary conditions. However, TIE relates to intensity derivatives along the optic axis, which cannot be directly measured.

These derivatives must be approximated using differences between intensity images on two adjacent planes, which is not in accordance with a relatively large separation between the planes to meet the phase-contrast requirement in the presence of noise. A mixed-phase retrieval method can directly combine CTF and TIE, and iteratively reconstruct phase shifts assuming a slowly varying absorption distribution. This algorithm alleviates the weak absorption assumption in CTF and the short propagation distance in TIE. To minimize the effect of measurement noise and enhance the accuracy of the conventional linear approximation model for X-ray in-line phase-contrast imaging, multiple intensity measurements at different distances from an object can be performed in the Fresnel diffraction region for reconstruction of a phase shift image.

X-ray small-angle scattering, or dark-field, imaging is used to acquire photons slightly deflected from the primary beam through an object. Small-angle scattering signals reflect structural texture on length scales between 1 nm to several hundred nanometers. This imaging mode can reveal subtle texture of tissues. For example, the growth of tumors causes remarkable differences of small-angle scattering patterns from that of healthy tissues. It is clinically important that the structural variation in tumors modifies the refractive index. The propagation of X-rays in a medium is characterized by the complex index of refraction. The cross-section of X-ray phase shift is one thousand times larger than that of linear attenuation in the 20-100 keV range. This means that phase-contrast imaging has much higher sensitivity for light elements than attenuation-contrast imaging. The contrast-to-noise ratio of differential phase contrast CT images is superior to the attenuation-contrast CT counterpart. Therefore, PCI can be used to observe unique critical structures of soft biological tissues. Moreover, the refractive index of a tissue is inversely proportional to the square of the X-ray energy while the absorption coefficient decreases as the fourth power of the X-ray energy. Hence, X-ray PCI is suitable to operate at higher energies (>30 keV) for lower radiation dose than attenuation imaging. Higher energy X-ray imaging is important for studies on large animals or patients.

Approximation models of the subject invention can be second-order approximation models for X-ray phase retrieval using paraxial Fresnel-Kirchhoff diffraction theory. An iterative method can be used to reconstruct a phase-contrast image (e.g., and in-line image) and a dark-field image.

To describe the X-ray and matter interaction at a specific wavelength of $\lambda$, an object can be characterized by a complex-valued refractive index distribution $n=1-\delta+i\beta$, where $\delta$ is for refraction, and $\beta$ is for attenuation. When a spatial coherent X-ray wave passes through an object, the X-ray wave front is deformed by variation of the refractive index in the object. $\delta$ ($10^{-6}$–$10^{-8}$) is about 1,000 times larger than $\beta$ ($10^{-9}$–$10^{-11}$) in biological soft tissues over the diagnostic radiation energy range. This implies that X-ray phase contrast imaging can achieve a higher signal-to-noise ratio at a lower radiation dose than attenuation contrast imaging. The wave-object interaction process can be described with a transmittance function $$T(r)=A(r)\exp[i\Phi(r)], \tag{36}$$

where r denotes transverse coordinates (x, y) in a transverse plane along the propagation direction z, A(r) is the amplitude modulus of the wave, and $\Phi(r)$ is the phase shift of the wave. The amplitude modulus and phase shift is related to the X-ray refractive index distribution $$A(r) = \exp\left[-\frac{2\pi}{\lambda}\int \beta(r,z)dz\right], \tag{37}$$

$$\Phi(r) = -\frac{2\pi}{\lambda}\int \delta(r,z)dz$$

Based on Fresnel-Kirchhoff diffraction theory, the wave field on the transverse plane in a free space is described by the Fresnel diffraction formula $$\mathcal{F}_z[T(r)] = \frac{|\exp(ikz)|}{i\lambda z}\int\int T(r')\exp\left(\frac{ik}{2z}|r'-r|^2\right)dr' \tag{38}$$

where $\mathcal{F}_z[T(r)]$ is the Fresnel diffraction pattern of the transmittance function at a distance of z from the object, and $k=2\pi/\lambda$ is a wavenumber. The Fourier transform of the Fresnel diffraction pattern at z can be formulated in terms of the autocorrelation of the transmittance function $$\int\int |\mathcal{F}_z[T(r)]|^2 \exp(-i2r\cdot w)dr = \tag{39}$$

$$\int\int\left\{A\left(r-\frac{\lambda z}{2}w\right)A\left(r+\frac{\lambda z}{2}w\right)\exp\left[i\Phi\left(r-\frac{\lambda z}{2}w\right)-i\Phi\left(r+\frac{\lambda z}{2}w\right)\right]\right\}$$

$$\exp(-i2\pi r\cdot w)dr$$

Hard X-ray radiation has a very short wavelength $\lambda$, and $\Phi(r)$ has only moderate variations for biological tissues. Thus, a second-order approximation to the exponential function of the phase in Equation (39) would be sufficiently accurate for practical applications $$\int\int |\mathcal{F}_z[T(r)]|^2 \exp(-i2\pi r\cdot w)dr = \tag{40}$$

-continued $$\int\int A\left(r-\frac{\lambda z}{2}w\right)A\left(r+\frac{\lambda z}{2}w\right)\left[1+i\Phi\left(r-\frac{\lambda z}{2}w\right)-i\Phi\left(r+\frac{\lambda z}{2}w\right)-\right.$$

$$\left.\frac{1}{2}\left(\Phi\left(r-\frac{\lambda z}{2}w\right)-\Phi\left(r+\frac{\lambda z}{2}w\right)\right)^2\right]\exp[-i2\pi r\cdot w)dr$$

Applying the autocorrelation formula to the parts involving A(r) and A(r)$\Phi$(r) on the right-hand side of Equation (40) respectively, $$\int\int [|\mathcal{F}_z[T(r)]|^2 - |\mathcal{F}_z[A(r)]|^2 - |\mathcal{F}_z[A(r)\Phi(r)]|^2]\exp(-i2\pi r\cdot w)dr = \tag{41}$$

$$\int\int A\left(r-\frac{\lambda z}{2}w\right)A\left(r+\frac{\lambda z}{2}w\right)\left[i\Phi\left(r-\frac{\lambda z}{2}w\right)-i\Phi\left(r+\frac{\lambda z}{2}w\right)-\right.$$

$$\left.\frac{1}{2}\Phi^2\left(r-\frac{\lambda z}{2}w\right)-\frac{1}{2}\Phi^2\left(r+\frac{\lambda z}{2}w\right)\right]\exp[-i2\pi r\cdot w)dr$$

Changing integral variables on the right-hand side of Equation (41), $$\int\int [|\mathcal{F}_z[T(r)]|^2 - |\mathcal{F}_z[A(r)]|^2 - |\mathcal{F}_z[A(r)\Phi(r)]|^2]\exp(-i2\pi r\cdot w)dr = \tag{42}$$

$$i\int\int [\exp(-i\pi\lambda z\cdot|w|^2)A(r+\lambda zw) - \exp(i\pi\lambda z\cdot|w|^2)A(r-\lambda zw)]$$

$$A(r)\Phi(r)\exp(-i2\pi r\cdot w)dr -$$

$$\frac{1}{2}\int\int [\exp(-i\pi\lambda z\cdot|w|^2)A(r+\lambda zw) + \exp(i\pi\lambda z\cdot|w|^2)A(r-\lambda zw)]$$

$$A(r)\Phi^2(r)\exp(-i2\pi r\cdot w)dr$$

During in-line phase-contrast imaging, phase contrast is manifested through a free-space propagation of a coherent X-ray beam, which transforms phase deformation on the object plane into intensity variation on an image plane. Equation (40) describes a relationship between measured intensity images and phase shifts. This model of the subject invention is plainly superior to the linear phase approximation model widely used for conventional X-ray in-line phase imaging, which assumes slow phase variation and weak linear attenuation of the object.

Dark-field imaging is also feasible along this direction. A dark-field image is formed through scattering of X-rays, which is sensitive to microstructures in the object. Boundaries and interfaces in biological tissues commonly produce strong dark-field signals. Hence, X-ray in-line dark-field imaging can be important to reveal detailed critical features of tissues. When a coherent X-ray beam goes through an object, X-ray photon scattering can change spatial coherence and transmitted intensity of X-rays, inducing a variation in the transmittance function $$T(r)=(Q(r)+\Delta Q(r))\exp[i(\Phi(r)+\Delta\Phi(r))], \tag{43}$$

where $\Delta\Phi(r)$ and $\Delta Q(r)$ are the phase and the amplitude variations on the object plane induced by scattered X-rays, respectively. Although the formulation itself in Equation (43) covers both small and large angle scattered photons, the main contributions should be from small angle scattering because the field of view for in-line imaging is typically small to satisfy the paraxial approximation assumption. The scattering effect would change the original transport path in the object, leading to an additional phase variation $\Delta\Phi$. The amplitude modulus A(r)=Q(r)+$\Delta$Q(r) on the object plane and the intensity I on an image plane can be measured respectively. Hence, from Equation (38), $$I = \left\| \frac{\exp(ikz)}{i\lambda z} \iint ((Q(r) + \Delta Q(r))\exp[i(\Phi(r) + \Delta \Phi(r))])\exp\left(\frac{ik}{2z}|r' - r|^2\right)dr' \right\|, \quad (44)$$

With a relative small variation $\Delta\Phi(r)$, the first-order approximation of $\exp(i\Delta\Phi(r))$ can be made to reduce Equation (44) to $$I = \left\| \frac{\exp(ikz)}{i\lambda z} \iint A(r)\exp[i\Phi(r)](1 + iD(r))\exp\left(\frac{ik}{2z}|r' - r|^2\right)dr' \right\| \quad (45)$$

where $$D(r) = \frac{\Delta Q(r)\Delta\Phi(r)}{A(r)}$$

represents a dark-field image to be reconstructed. The phase image $\Phi(r)$ can be recovered using the method described herein. Hence, the dark-field image $D(r)$ can be reconstructed from intensity measurements, based on Equation (45).

In an embodiment, an iterative method can be used for phase reconstruction (e.g., based on Equation 42). The method can include Equations (46) below.

$$i \iint [\exp(-i\pi\lambda z \cdot |w|^2)A(r + \lambda zw) - \exp(i\pi\lambda z \cdot |w|^2)A(r - \lambda zw)] \quad (46)$$

$$\exp(-i2\pi r \cdot w)p_{k+1}(r)dr =$$

$$\iint [|\mathscr{F}_z[T(r)]|^2 - |\mathscr{F}_z[A(r)]|^2 - |\mathscr{F}_z[p_k(r)]|^2]\exp(-i2\pi r \cdot w)dr +$$

$$\frac{1}{2}\iint \left[\exp(-i\pi\lambda z \cdot |w|^2)\frac{A(r + \lambda zw)}{A(r)} + \exp(i\pi\lambda z \cdot |w|^2)\frac{A(r - \lambda zw)}{A(r)}\right]\exp(-i2\pi r \cdot w)p_k^2(r)dr$$

$$p_0(r) = 0, \; p_k(r) = A(r)\Phi_k(r), \; k = 0, 1, \ldots,$$

where $|\mathscr{F}_z[T(r)]|^2$ is the measurement on the Fresnel diffraction pattern at a distance z, $|\mathscr{F}_z[A(r)]|^2$ is the measurement on the object plane, $\mathscr{F}_z[A(r)]|^2$ gives the modulus of the function $p_k(r)$. Equation (46) can be discretized to a system of linear equations with respect to variables $p_k(r)$. Then, the algebraic reconstruction technique (ART) can be employed for phase image reconstruction. ART is a widely-used iterative method for its robustness and efficiency.

In the iterative scheme, the absorption term is accurate without any approximation. Hence, no limitation is imposed on the attenuation property of an object. The exponential function of phase variation has been approximated to the second order, which should be very accurate for hard X-ray imaging. Therefore, the second-order phase models of the subject invention can be very informative and useful for biomedical imaging. The second-order model can be computationally complex, and can have a high computational cost under certain circumstances. With the development of high-performance computing techniques, especially Graphics Processing Units (GPUs), any computational issues should not be a problem.

X-ray in-line imaging can have higher spatial resolution than X-ray grating-based imaging. The field of view for in-line imaging ought to be small to satisfy the paraxial approximation requirement, and yet practical applications often focus on a small region of interest (ROI) in an object. Therefore, interior tomographic imaging methods would be useful to deliver unique and stable ROI reconstructions from truncated projection data.

The second-order phase approximation models for X-ray phase retrieval, and iterative algorithms, can be used for both in-line phase-contrast and dark-field imaging. These models accurately establish quantitative correspondence between phase shifts and image intensities, outperforming the related art linear phase approximation model used for X-ray in-line phase contrast imaging, because the linear model assumes slow phase variation and weak linear attenuation of an object. The iterative method can incorporate the state of the art compressive sensing techniques to achieve high quality image reconstruction.

In an embodiment, a system can include a machine-readable medium (e.g., a computer-readable medium) having machine-executable instructions (e.g., computer-executable instructions) for performing a method of reconstructing an image (e.g., an X-ray image), the method comprising using a second-order approximation model as described herein. The machine-readable medium (e.g., computer-readable medium) can be non-transitory (e.g., a non-transitory computer-readable medium).

In an embodiment, a method of performing imaging (e.g., X-ray PCI) can include providing an imaging system (e.g., X-ray PCI system) as described herein, positioning an object to be imaged in the appropriate location within the system (e.g., between the energy source and the period-varying grating), and imaging the object using the system. In a further embodiment, the method can include using a second-order approximation model as described herein to reconstruct the image (e.g., X-ray image).

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

An imaging system, comprising:
an energy source;
a detector;
a first grating disposed between the energy source and the detector; and
a second grating disposed between the first grating and the detector,
wherein the first grating is a quasi-periodical grating (such that the period of the grating varies across the grating (e.g., in a lateral direction across the grating)).

Embodiment 2

The system according to embodiment 1, wherein the first grating is a quasi-periodical phase grating.

Embodiment 3

The system according to any of embodiments 1-2, wherein the second grating is an analyzer grating.

Embodiment 4

The system according to any of embodiments 1-3, wherein the detector is flat.

Embodiment 5

The system according to any of embodiments 1-4, wherein the detector is a flat detector array.

Embodiment 6

The system according to any of embodiments 1-3, wherein the detector is curved (such as cylindrical (e.g., curved like a portion of a cylinder) or spherical (e.g., curved like a portion of a sphere)).

Embodiment 7

The system according to any of embodiments 1-6, wherein the second grating is flat.

Embodiment 8

The system according to any of embodiments 1-6, wherein the second grating is curved (such as cylindrical (e.g., curved like a portion of a cylinder) or spherical (e.g., curved like a portion of a sphere)).

Embodiment 9

The system according to any of embodiments 1-8, wherein the first grating is flat.

Embodiment 10

The system according to any of embodiments 1-8, wherein the first grating is curved (such as cylindrical (e.g., curved like a portion of a cylinder) or spherical (e.g., curved like a portion of a sphere)).

Embodiment 11

The system according to any of embodiments 1-10, further comprising a source grating disposed between the energy source and the first grating.

Embodiment 12

The system according to any of embodiments 1-11, wherein the source grating is flat.

Embodiment 13

The system according to any of embodiments 1-11, wherein the source grating is curved (such as cylindrical (e.g., curved like a portion of a cylinder) or spherical (e.g., curved like a portion of a sphere)).

Embodiment 14

The system according to any of embodiments 1-13, wherein the imaging system is an X-ray phase-contrast imaging (PCI) system, and wherein the energy source is an X-ray source.

Embodiment 15

The system according to any of embodiments 11-14, wherein the system is configured such that an object to be imaged is positioned between the source grating and the first grating while it is being imaged.

Embodiment 16

The system according to any of embodiments 1-15, wherein the system is configured such that an object to be imaged is positioned between the energy source and the first grating while it is being imaged.

Embodiment 17

The system according to any of embodiments 1-16, wherein the first grating has a slow-varying period.

Embodiment 18

The system according to any of embodiments 1-17, wherein the period of the first grating varies the same way in both lateral directions moving away (e.g., as the angle is varied positively or negatively by the same amount) from a point on the first grating where radiation from the energy source is centered during imaging (see, e.g., FIGS. 3A and 11C).

Embodiment 19

The system according to any of embodiments 1-18, wherein the second grating matches the curvature (or lack thereof) of the detector.

Embodiment 20

A method of reconstructing or retrieving an image, the method comprising:

using a second-order approximation model using paraxial Fresnel-Kirchhoff diffraction theory as described herein.

Embodiment 21

The method according to embodiment 20, further comprising performing an iterative method to reconstruct a phase-contrast image and/or a dark-field image.

Embodiment 22

The method according to any of embodiments 20-21, further comprising iteratively solving the model using the algebraic reconstruction technique (ART).

Embodiment 23

The method according to any of embodiments 20-22, further comprising incorporating state of the art compressive sensing techniques to achieve high quality image reconstruction.

Embodiment 24

The method according to any of embodiments 21-23, wherein the iterative method is based on Equation (42) herein Embodiment 25

The method according to any of embodiments 21-24, wherein the iterative method includes Equation (46) herein.

Embodiment 26

The method according to embodiment 25, further comprising discretizing Equation (46) to a system of linear equations with respect to variables $p_k(r)$.

Embodiment 27

The method according to embodiment 26, further comprising employing the ART for phase image reconstruction.

Embodiment 28

The method according to any of embodiments 20-27, wherein the image is an X-ray phase image.

Embodiment 29

A machine-readable medium (e.g., a computer-readable medium) having machine-executable instructions (e.g., computer-executable instructions) for performing the method according to any of embodiments 20-28.

Embodiment 30

The machine-readable medium according to embodiment 29, wherein the machine-readable medium is non-transitory (e.g., a non-transitory computer-readable medium).

Embodiment 31

A system comprising the machine-readable medium according to any of embodiments 29-30.

Embodiment 32

A method of performing imaging, comprising:

providing the imaging system according to any of embodiments 1-19;
positioning an object to be imaged in the appropriate location within the system (e.g., between the energy source and the first grating); and
imaging the object using the system.

Embodiment 33

The method according to embodiment 32, further comprising performing the method according to any of embodiments 20-28 to reconstruct and/or retrieve an X-ray image (e.g., an in-line and/or dark-field image).

Embodiment 34

The method according to embodiment 33, wherein the method according to any of embodiments 20-28 is performed using the machine-readable medium according to any of embodiments 29-30 or the system according to embodiment 31.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

A numerical analysis was performed to show the modified interference pattern along the x-axis parallel to the grating plane for both a constant-period grating and a period-varying phase grating according to an embodiment of the subject invention. In this analysis, a pure phase grating with a $\lambda$ phase shift was illuminated by a fully coherent parallel-beam of 28 keV.

Figure 3B:
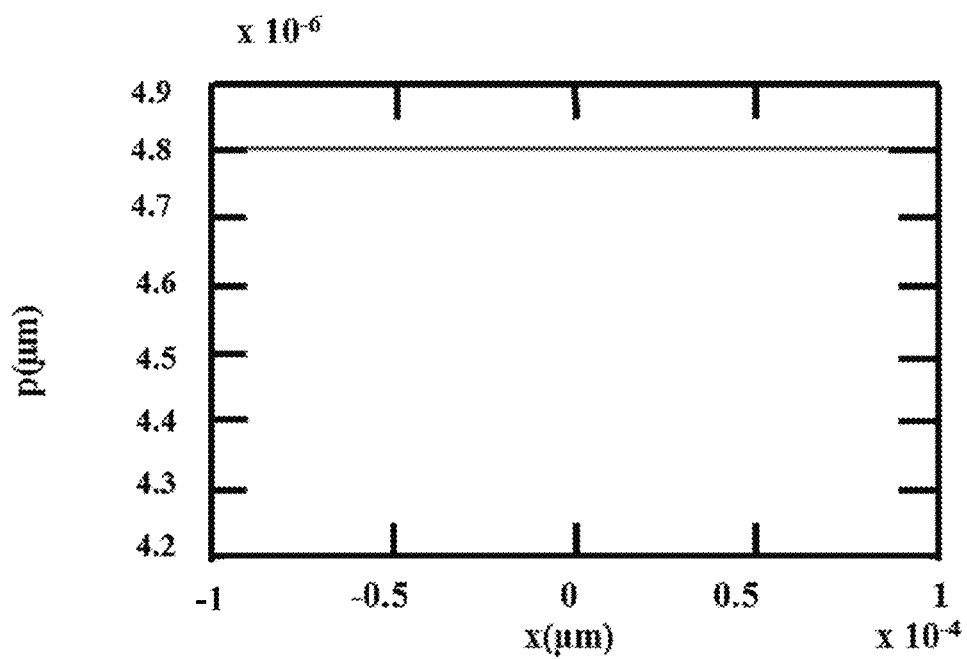
FIG. 3B shows a plot of period along the x-axis for a constant-period grating.
Figure 3C:
FIG. 3C shows the interference pattern for the grating used for the plot of FIG. 3A.
Figure 3D:
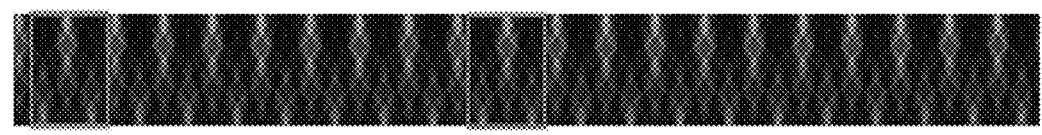
FIG. 3D shows the interference pattern for the grating used for the plot of FIG. 3B.
Figure 3E:
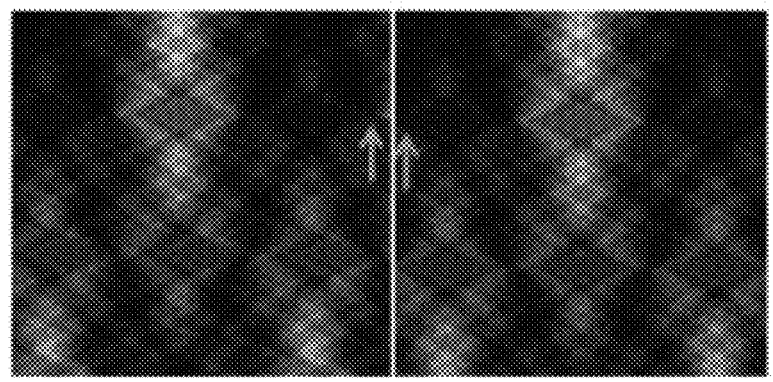
FIG. 3E shows enlarged versions of the two highlighted sections in FIG. 3D.

FIG. 3A shows a plot of the period (in μm) along the x-axis (in μm) for the period-varying phase grating. FIG. 3B shows a plot of the period (in μm) along the x-axis (in μm) for the constant-period grating. FIG. 3C shows the interference pattern at different propagation distances from the grating for the period-varying phase grating. FIG. 3D shows the interference pattern at different propagation distances from the grating for the constant-period grating. FIG. 3E shows an enlarged view of the two boxes highlighted in FIG. 3D. The red arrows in FIG. 3E show the difference caused by the grating aperture widths (plotted in FIG. 3A).

Example 2

To analyze the Talbot self-imaging performances with different combinations of gratings and detectors, as well as with periodic and quasi-periodic gratings designs, numerical experiments were performed.

The energy of incident X-rays was set to 28 keV. The distance between the X-ray source and the phase grating G1 grating was 1 m, the phase grating G1 and absorption grating G2 were separated by the first-order fractional Talbot distance, calculated according to Equation (10). The period of the phase grating G1 ($p_{G1}$ was 4.8 μm, while the period of the absorption grating G2 ($p_{G2}$) was determined according to imaging geometry. In the data collection step, the classic phase stepping method was employed, and the visibility of the stepping curve was used to quantify the imaging performance. The detector cell pitch was 50 µm.

First, for a grating-based phase-contrast imaging system, if the detector and the absorption grating have different curvatures as indicated by the red arrows in FIGS. 4B and 4C, there would be non-uniform gaps to the detector. The non-uniform gap distribution would introduce non-uniform image artifacts due to the blurring effect from the X-ray spot. Therefore, a better or optimal design would place the absorption grating G2 with as closely aligned curvature or shape as possible to that of the detector plane, leading to the grating-detector system designs illustrated in FIGS. 4A and 4D.

Due to the imperfect fabrication of the gratings and/or difficulty in matching the gratings to the beam divergence, the phase grating G1 and absorption grating G2 may not be able to be exactly paired, as shown in FIG. 5, where curved G1 and flat G2, or flat G1 and curved G2 are assumed for optimized PCI system designs, as shown in FIG. 6A. In a conventional grating-based PCI system, a periodic phase grating is adopted to produce the same interference patterns at a Talbot length. However, in FIGS. 5A and 5B the phase grating and absorption grating are not paired, which means that the absorption grating cannot be located exactly on the interference patterns.

FIG. 5A shows a schematic view of a grating-based phase-contrast system with a curved G1 and a flat G2 (and flat detector). FIG. 5B shows a schematic view of a grating-based phase-contrast system with a flat G1 and a curved G2 (and curved detector). FIG. 5C shows a plot of the visibility versus angle (in degrees) for the setup of FIG. 5A. FIG. 5D shows a plot of the visibility versus angle (in degrees) for the setup of FIG. 5B.

FIG. 6A shows a plot of visibility versus angle (in degrees) for the unpaired G1-G2 system of FIG. 5A and a period-unmatched imaging system. The red line (upper line) is for the period-unmatched system, and the blue line (lower line) is for the system of FIG. 5A). FIG. 6B shows a plot of visibility versus angle (in degrees) for the period-matched imaging system.

Example 3

To demonstrate the performance of the quasi-periodic grating, numerical simulations with Matlab (Mathwork) were conducted for both curved periodic phase grating G1 and quasiperiodic phase grating G1' based on the general setup shown in FIG. 10B. In the simulation, the energy of the X-ray beam was 28 keV. The period of the phase grating G1 was set to 4.8 µm, with a radius, $r_0=1.0$ m. The center of planar analyzer (absorption) grating G2 was at the first fractional Talbot image of the center of G1. $1/r_D - 1/r_0 = p^2/8\lambda r_0^2$. G1' had the central period set to be the same as G1. The calculated period of G1' as a function of θ is shown in FIG. 11C, and the period of G2' is calculated accordingly.

The period of the quasi-periodic grating is larger than 4.8 µm, and the same fabrication process for periodic grating can be adapted (see, e.g., David et al., "Fabrication of diffraction gratings for hard X-ray phase contrast imaging," Microelectron. Eng. 84(5-8), 1172-1177 (2007), which is incorporated by reference herein in its entirety). The pixel size of the detector was set to 24 µm, five times the period of G1.

Figure 11A:
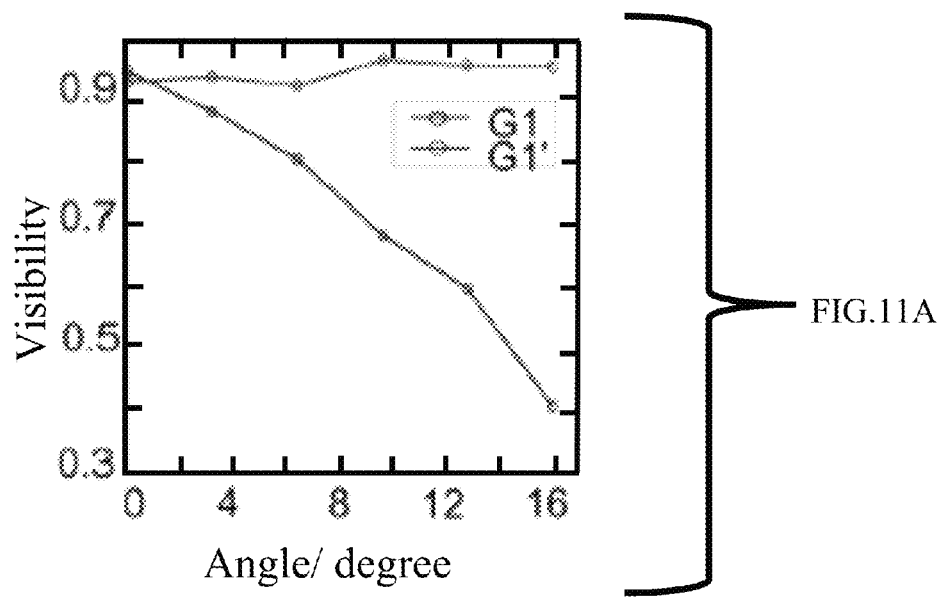
FIG. 11A shows a plot of visibility versus angle.
Figure 11B:
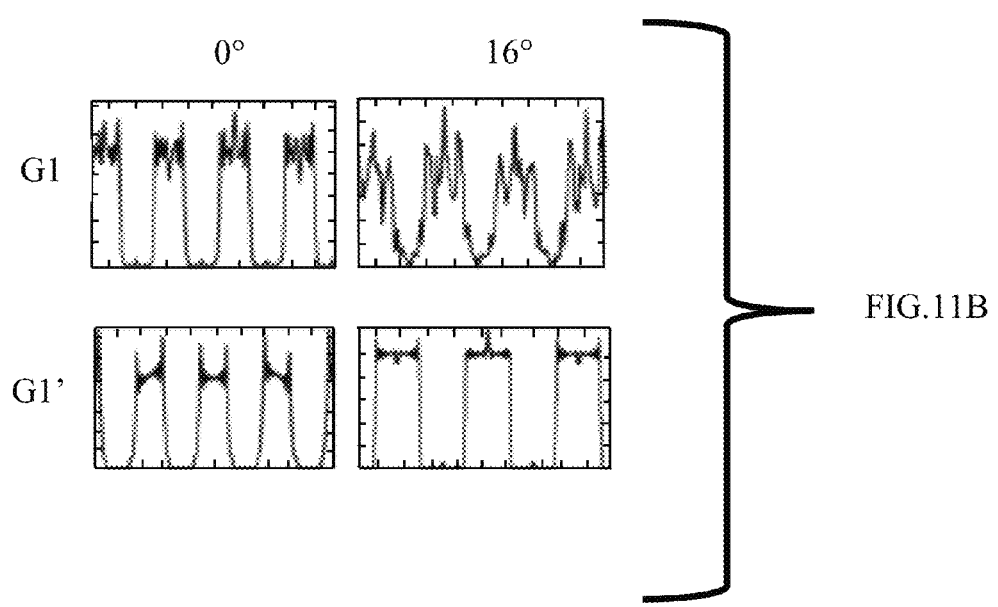
FIG. 11B shows intensity profiles for phase gratings.
Figure 11C:
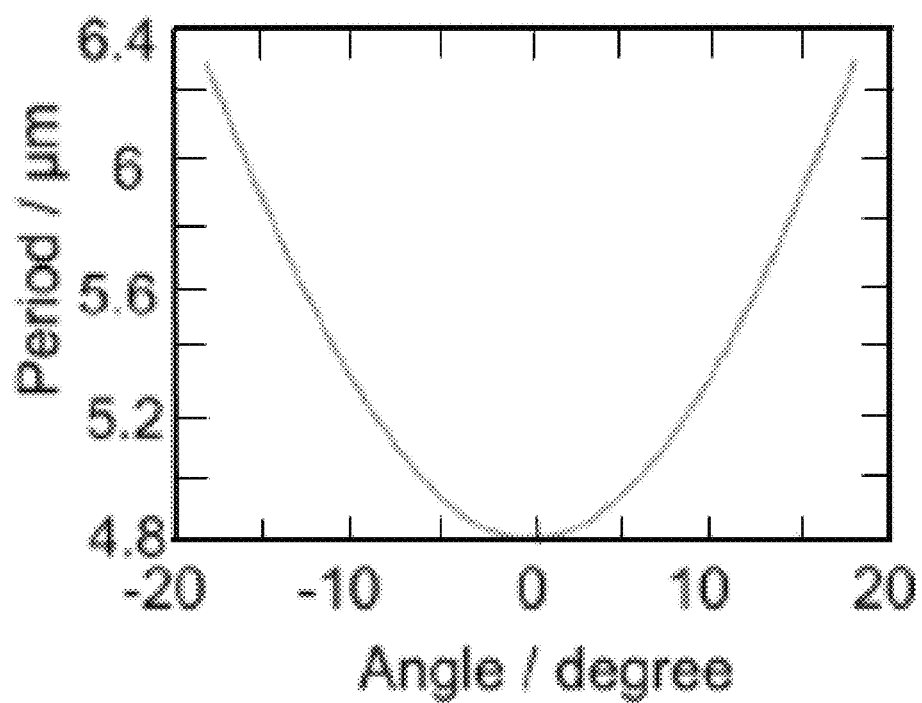
FIG. 11C shows a plot of period versus angle for a quasi-periodic phase grating according to an embodiment of the subject invention.

FIG. 11A shows a plot of visibility versus angle (in degrees) for the simulations in the X-ray regime. The red line (uppermost line) is for G1' (quasi-periodic phase grating), and the blue line (lower most line sloping downward) is for G1. FIG. 11B shows intensity profiles at the first fractional Talbot distance of both G1 and G1' at 0° and 16°. The upper-left is for G1 at 0°; the upper-right is for G1 at 16°; the lower-left is for G1' at 0°; and the lower-right is for G1' at 16°. FIG. 11C shows a plot of the period (in µm) versus the angle (in degrees) for the quasi-periodic phase grating G1'.

The visibility of the stepping curves at first fractional Talbot distance G1 and G1' are shown in FIG. 11A. Referring to FIGS. 11A-11C, a decrease of 58% in visibility for G1 at 16° was observed, while no obvious decrease was observed in the visibility for G1'. The source in the X-ray regime is not truly an absolute point source. The intensity of a fringe pattern can be expressed as a convolution of the intensity profile of the source and the fringe pattern of an ideal point source. This convolution will decrease the visibility of the fringes pattern. This is always an issue in the X-ray regime for both quasi-periodic and periodic gratings. If necessary, a G0 grating can be used for needed spatial coherence.

Example 4

To experimentally verify the analysis of Example 3, experiments were designed in the visible optical regime. Numerical simulations were also conducted. Different from the X-ray simulation, G1 was set as an absorption grating. G2 was separated from G1 by one Talbot distance. The wavelength of the source, λ, was 0.67 µm to match the optical experiment setup. The period of G1, $p_0$, was set to be 91 µm with a radius, $r_0=75$ mm. The quasi-periodic grating G1' had the central period set to be the same as that of G1. Given that G1' had the same radius as G1, Equation (34) and Equation (35) were used to calculate its period p ranging from −30° to 30°. The calculated period of G1' as a function of θ is shown in FIG. 12C.

The diagram of the experimental setup is shown in FIG. 13A. The point source came from a laser with fiber coupled output (Suprlum, SLD-261, λ=670 nm). The driven current was set at 133 mA (Suprlum, pilot-2). Two lenses (f1=100 mm, f2=62.9 mm) were used to relay a relayed focal point of 41.0°. The radius of the acrylic tube was 75 mm. The periodic grating and the quasi-periodic grating with central period of 91 µm were made on a mylar film with a thickness of 180 µm (CAD/Art Services, Inc.), which could be bent easily. Two gratings were taped on the outer surface of the acrylic tube. The detection microscope system included a microscope objective (Nikon, 10X/0.3), a tube lens (f=200 mm), and a CMOS camera (JAI, GO5000M), all of which were installed on a motorized translation stage (Thorlab, NRT-100). A stepper motor controller (Thorlab, apt) drove the stage, so that the detection system was able to scan the field in the x direction. The scan range of the experiment was 50 mm, with 5 mm step size, covering an angular range from −13° to 13°. The microscope objective could adjust its focus in the y direction. The plane with the highest fringes contrast near the calculated Talbot distance was set as the observation plane.

Figure 12A:
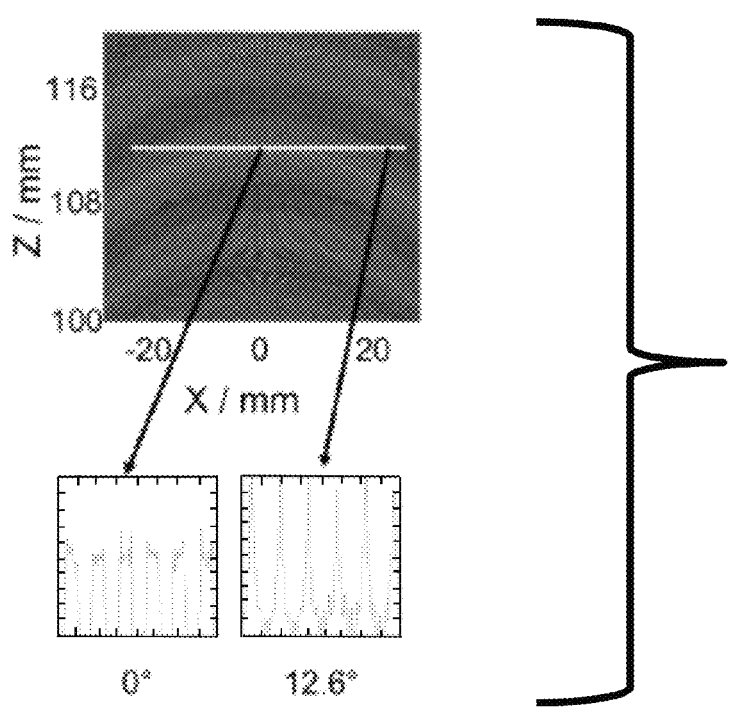
FIG. 12A shows a Talbot carpet of a periodic grating.
Figure 12B:
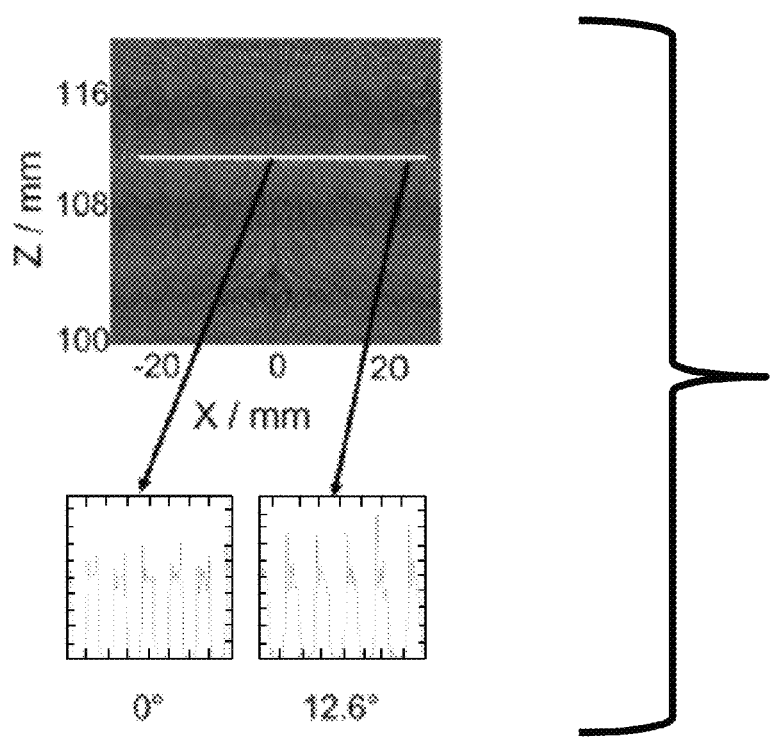
FIG. 12B shows a Talbot carpet of a quasi-periodic grating G1' according to an embodiment of the subject invention.
Figure 12C:
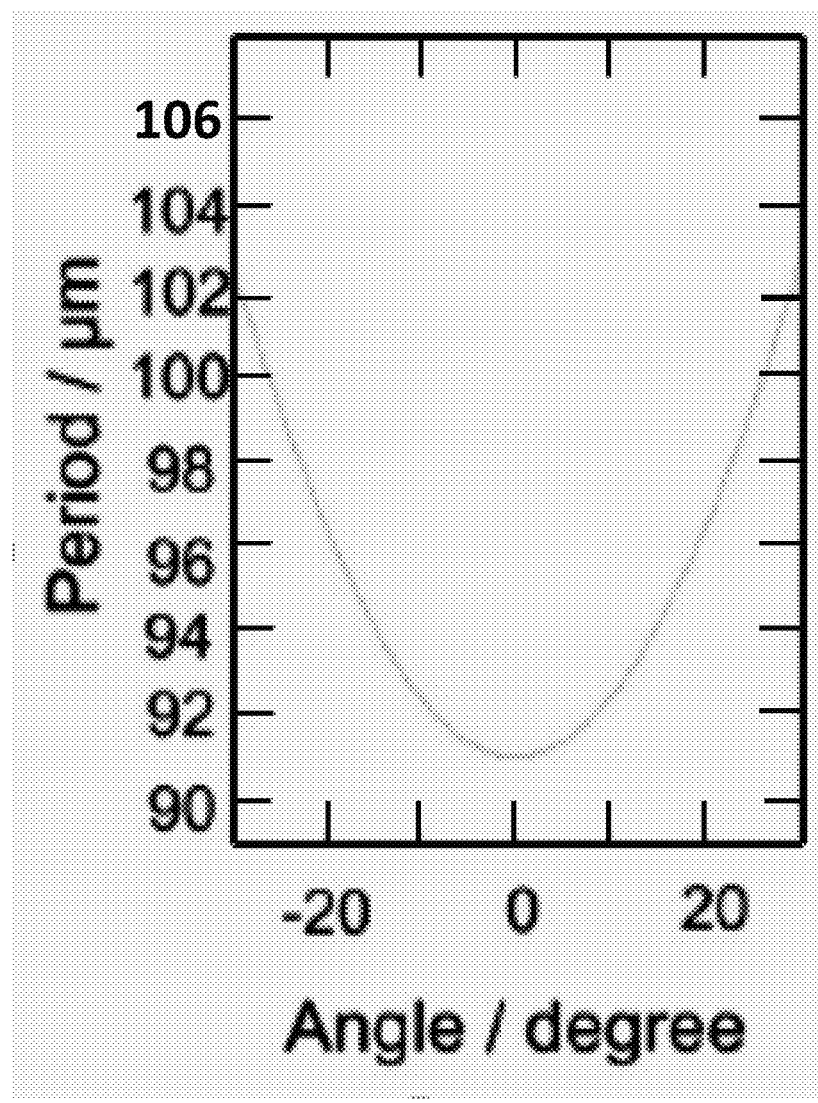
FIG. 12C shows a plot of period versus angle.

FIG. 12A shows the Talbot carpet of the periodic grating G1; the vertical axis is Z (in mm), and the horizontal axis is X (in mm). The period of the grating was 91 µm. The blown-up portions are for 0° and 12.6°. FIG. 12B shows the Talbot carpet of the quasi-periodic grating G1'; the vertical axis is Z (in mm), and the horizontal axis is X (in mm). The period of the grating at the X=0 line was 91 µm. The blown-up portions are for 0° and 12.6°. FIG. 12C shows a plot of the period (in µm) versus the angle (in degrees) for the quasi-periodic phase grating G1'. The period was calculated from Equation (35). These results are from the simulations in the visible optical regime. The wavelength of the source was 0.67 µm; the radius of the grating was 75 mm; and the white line in both FIGS. 12A and 12B, indicating the self-imaging plane, was located at Y=111.9 mm. The Talbot carpets are shown in Cartesian coordinates. It can be observed that the self-imaging surface of grating G1 is on a curved plane. FIG. 12B shows that the self-imaging surface of the quasi-periodic grating G1' is almost flat. The ideal Talbot image is located at $r_D$=111.9 mm. If a flat array detector were placed at this plane, indicated by the white solid lines in FIGS. 12A and 12B, the interference fringes would be distorted at 12.6° for periodic grating G1, while the fringes maintain the original fringe profiles for the quasiperiodic grating G1'.

FIG. 13A shows a schematic view of the experimental setup. S is the point source $\lambda$=0.67 µm. A periodic grating G1 or quasi-periodic grading G1' is fixed on a cylindrical surface. P denotes the observation plane; Obj denotes the microscope objectives; L denotes the tube lens; and D denotes the CMOS detector. FIG. 13B shows images of interference fringes at 0° on the observation plane. FIG. 13C shows images of interference fringes at 7.4° on the observation plane. FIG. 13D shows images of interference fringes at 12.24° on the observation plane.

In these optical experiments, the fields were scanned along the x-axis. The images acquired by the CMOS camera at 0°, 7.4°, and 12.2° angles from G1 and G1' are shown in FIGS. 13B-13D, respectively. The results also show that the fringes from the periodic grating G1 had a severe distortion at larger angles, while those from the quasi-periodic grating G1' did not change much or at all.

Figure 14:
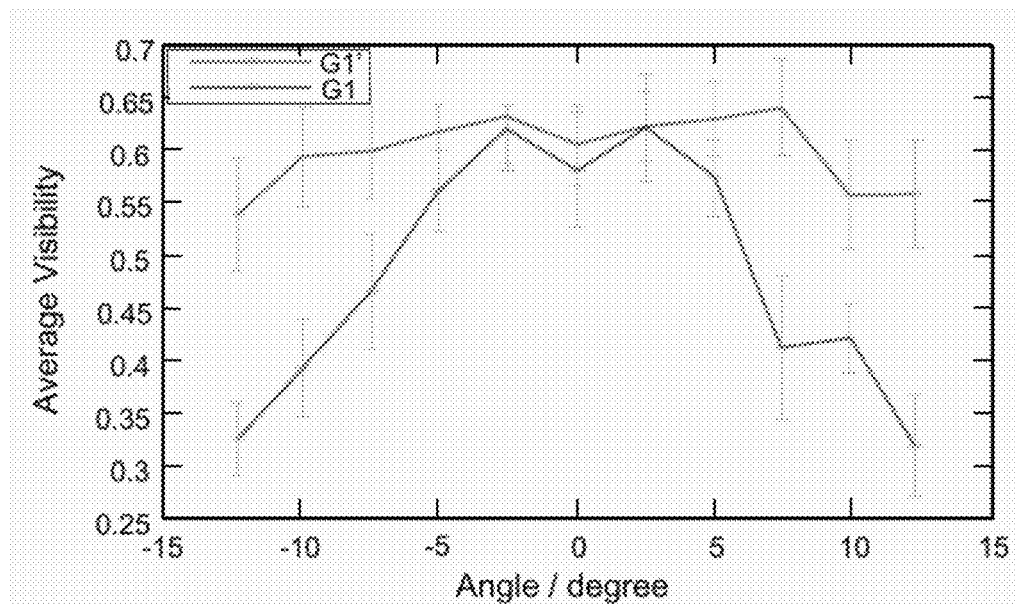
FIG. 14 shows a plot of average visibility versus angle for a periodic grating and a quasi-periodic grating on the observation plane.

In the X-ray PCI setups, the pixel size of the detector was ~5 times larger than the period of G1, and the analyzer grating G2 should resolve the lateral shifts of the fringes. In this experiment, the effective pixel size of the CMOS camera after the microscope magnification (~0.5 µm) was less than the period of fringes on the observation plane. In order to compare the experimental results, the images were processed to add in a 'virtual' analyzer grating G2. The readout from a virtual pixel consists of five periods of the fringes. Because for quasi-periodic grating the periods have slight variance with respect to the angle, the period of G2' is calculated accordingly at the observation plane. The virtual grating G2 and G2' scan 40 phase steps for one period of the fringes. FIG. 14 shows the experimental visibility of the periodic grating G1 and quasi-periodic grating G1'. The visibility was calculated from averaging the visibility from 100 sub-regions with 3 mm in width and 2 µm in height on the CMOS camera.

FIG. 14 shows a plot of average visibility versus angle (in degrees) for the periodic grating G1 and the quasi-periodic grating G1' on the observation plane. The red line (upper line) is for G1', and the blue line (lower line) is for G1. It can be observed that the quasi-periodic grating G1' maintains a uniform (or nearly uniform) visibility on the observation plane. From −13° to 13°, the visibility variance of G1' is less than 10%, while the visibility for G1 dropped by over 10% after only 5° from center.

Example 5

The results in Example 4 show an overall decrease in the visibility. Three reasons could possibly have caused this difference: the speckle noise; low contrast of the binary mask; and the optical aberration from the mask film.

First, a coherent source was used in Example 4, which introduced laser speckles to the measurement. In addition, the artifacts on the grating surface can contribute to the blur of the interference fringes. From the measured images of the fringes, the average size of the speckles was ~13 µm, and the standard deviation of the intensity was 30%. These artifacts, coupling the light to the non-harmonic frequency components of the fringes, can reduce the experimental visibility.

Second, the opaque part of the grating was not strictly dark in Example 4. The opaque region had a measured intensity of ~10% of the maximum intensity, which essentially acted as a bias to the field. This low contrast of the grating mask can also decrease the visibility.

Third, due to the mask printing process, the thickness of the transparent region was not completely uniform in Example 4. A profilemeter measured the average difference of the thickness to be ~0.13 µm. This non-uniform thickness of the mask can introduce a lensing effect. Evidence for this speculation is that the field distribution along the Talbot distance was asymmetric. This aberration effect can also affect the visibility.

The three aforementioned effects were incorporated into the simulation in this example. Specifically, to include the speckle noise, the images were divided into small regions with a size of 13 µm, and random Gaussian noise with a standard deviation of 30% of the local intensity was added to each region. The transmittance bias and the lensing effect were also included in the simulation.

Figure 15A:
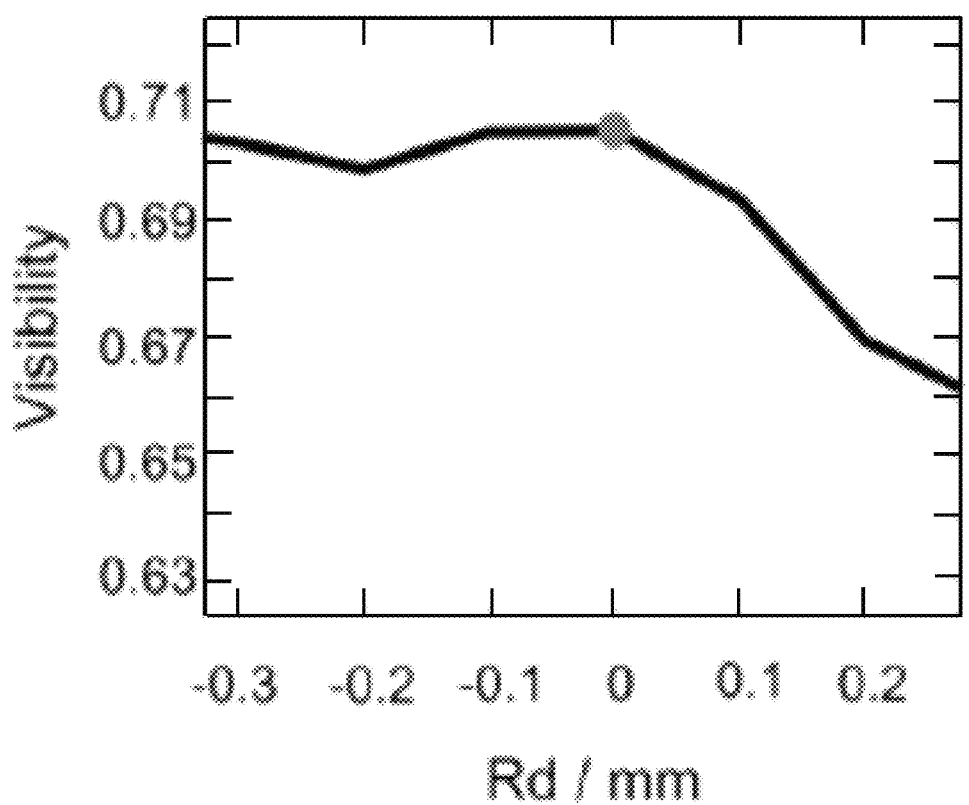
FIG. 15A shows a plot of visibility versus the radius direction of the periodic grating for a simulated visibility profile.
Figure 15B:
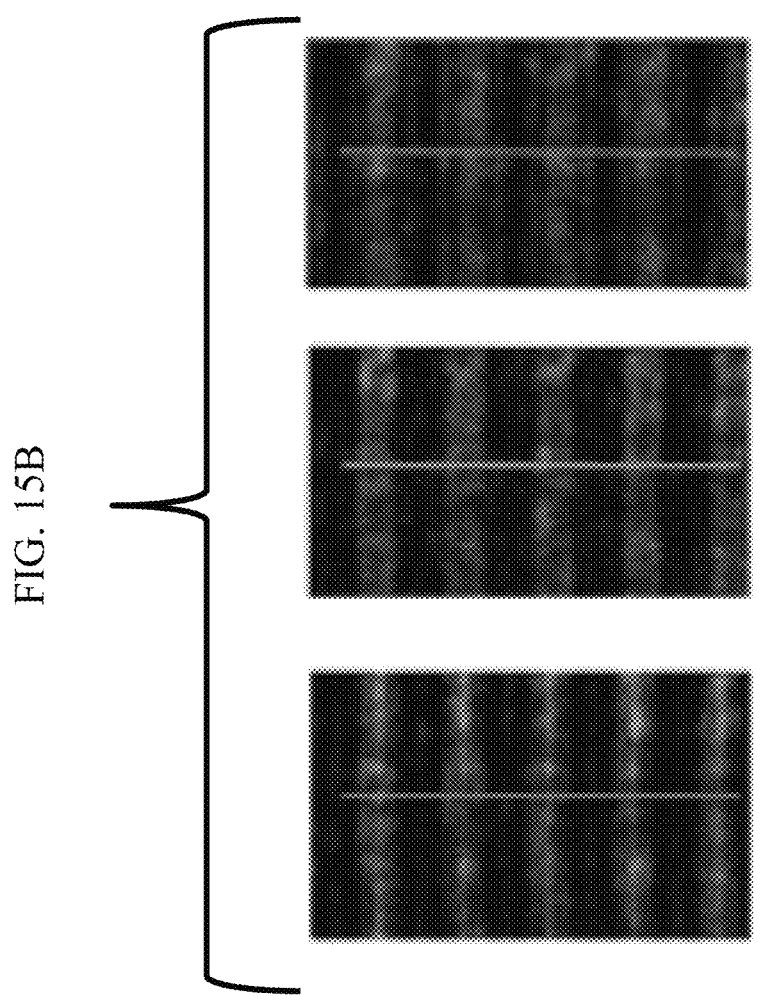
FIG. 15B shows experimental images of interference fringes.
Figure 15C:
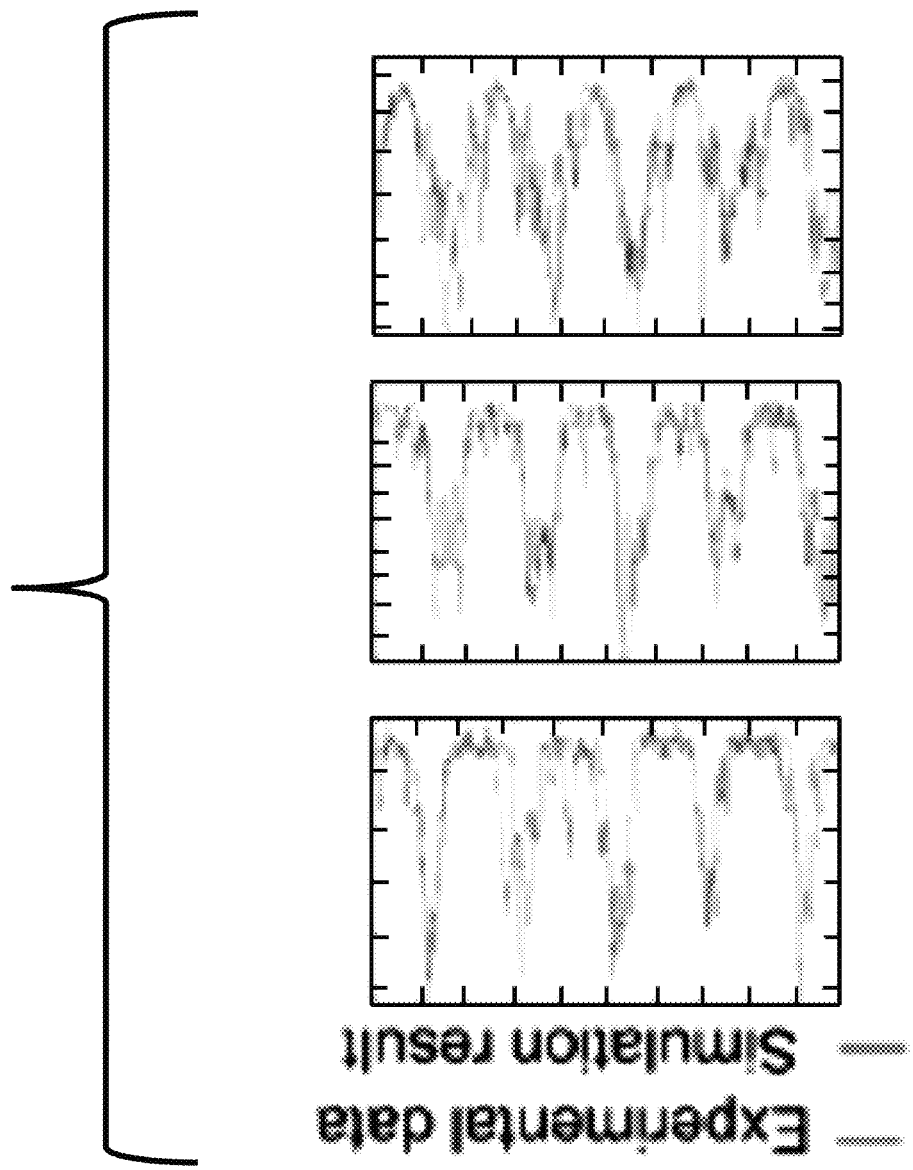
FIG. 15C shows profiles of interference fringes.

FIG. 15A shows a plot of visibility versus the radius direction of the periodic grating (in mm) for the simulated visibility profile. The origin was set at the observation plane. FIG. 15B shows experimental images of interference fringes at −2 mm (top image), 0 mm (middle image), and 2 mm (bottom image) from the observation plane. FIG. 15C shows profiles of interference fringes. The red curves denote simulated profiles, and the blue curves denote the grayscale value profiles of the blue (near the center) lines marked in FIG. 15B. The profiles are for −2 mm (top profile), 0 mm (middle profile), and 2 mm (bottom profile).

The simulated visibility is shown in FIG. 15A. The red point marks the observation plane. The visibility curve, as predicted, was asymmetric from the observation plane. The visibility at the red point was 0.7, which was close to the peak visibility in the experiment. The intensity pattern was measured at −2 mm, 0 mm, and 2 mm away from the observation plane. The experimental images are shown in FIG. 15B. The simulated and experimental intensity profiles of the interference fringes are shown in FIG. 15C.

The ratio between the grating period and the wavelength, $p/\lambda$, is on the order of $10^4$ in the X-ray regime, and $p/\lambda$ is on the order of $10^2$ for the experiment in the visible regime, and both of these are sufficiently large for the approximation in Equations (21) and Equation (22) to be valid.

Example 6

Figure 7A:
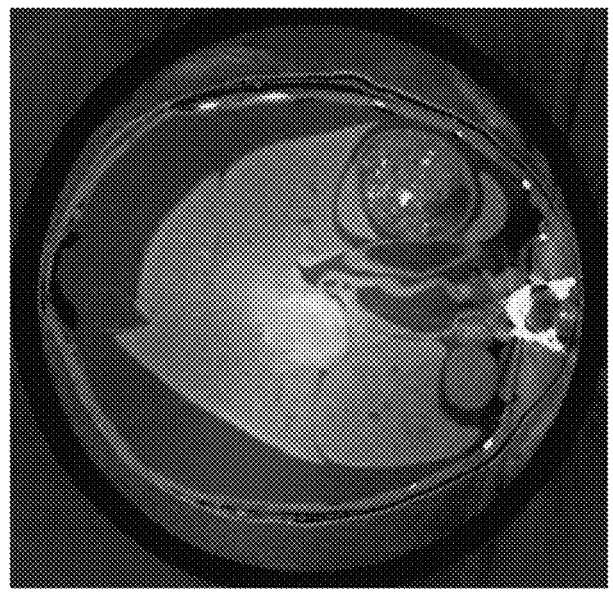
FIG. 7A shows a true phase image.
Figure 7B:
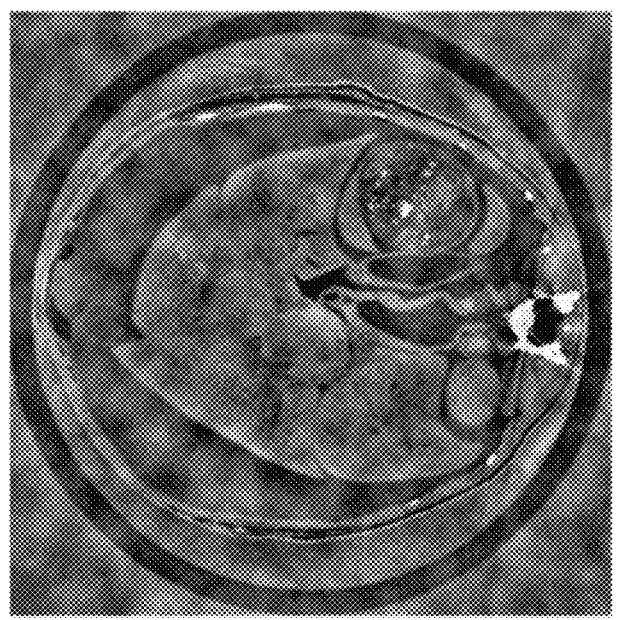
FIG. 7B shows a reconstructed version of the image of FIG. 7A, according to an embodiment of the subject invention.
Figure 7C:
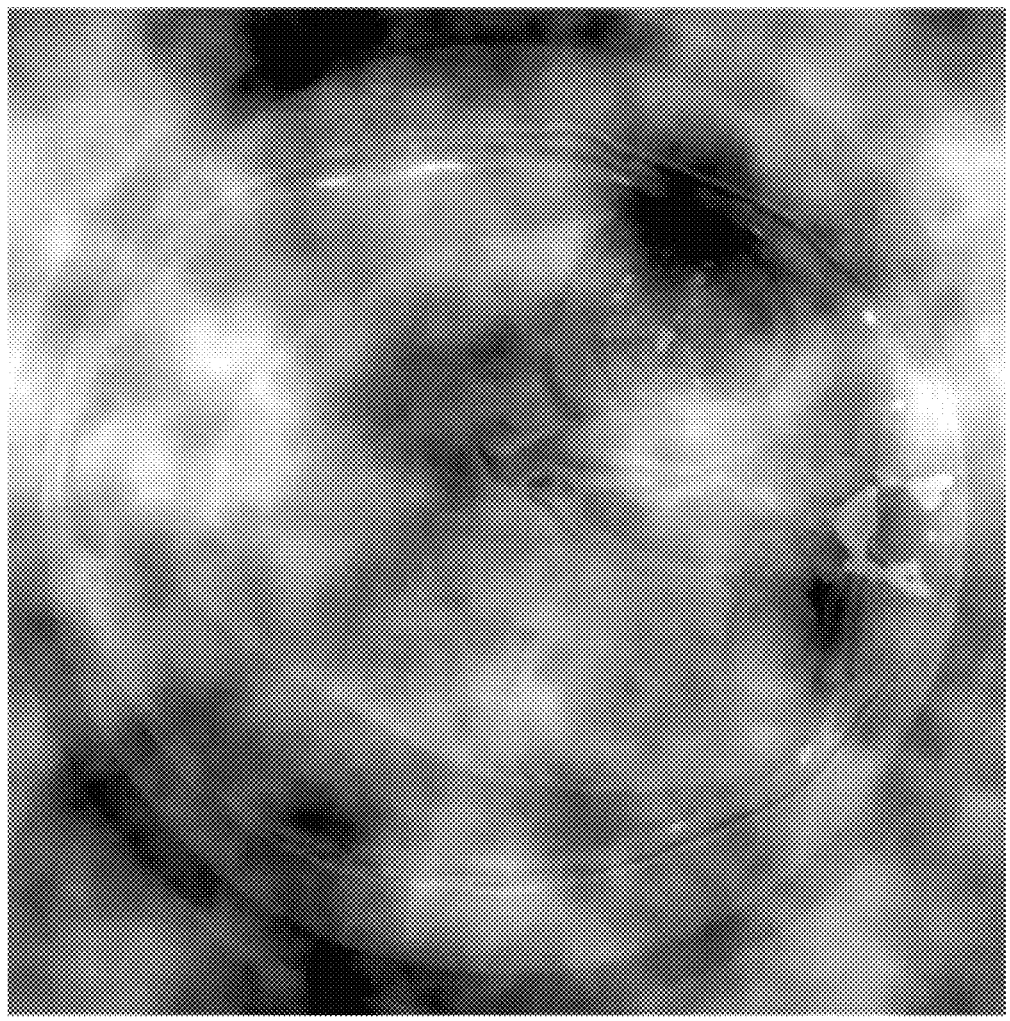
FIG. 7C shows a reconstructed version of the image of FIG. 7A, according to a related art reconstruction method.

Numerical tests were performed to demonstrate the feasibility of second-order approximation models for X-ray phase retrieval described herein (see, e.g., Equations (36)-(45)). The phase contrast image shown in FIG. 7A was used as the phase distribution after the wave-object interaction. FIG. 7A shows the true phase image. FIG. 7B shows a reconstructed version of the image of FIG. 7A, reconstructed using a method of the subject invention. FIG. 7C shows a reconstructed version of the image of FIG. 7A, reconstructed using a related art TIE-based reconstruction method. The image of 7A is from https://www.maxlab.lu.se/sv/MED-MAX.

The phase image had 498×500 pixels with a pixel size of 3 μm. The radiation wavelength was set to λ=0.25 Å, corresponding to hard X-rays. It was assumed that the intensity distribution on the object plane was uniform to mimic a homogeneous attenuation scenario. The wave amplitudes on the transverse plane through free space propagation can be simulated using the Fresnel transform Equation (38). The intensity distribution on the image plane at a propagation distance of 1000 mm was calculated, with Poisson noise added to the intensity image. Equation (43) was discretized into a system of linear equations, and the ART algorithm was employed to reconstruct the phase image. The procedure took 4 iterations to produce the phase contrast image as shown in FIG. 7B. For the comparison, the phase reconstruction was performed using the TIE-based reconstruction method. The same image plane and the same Poisson noise were used, and the differences between the intensity images on the object and image planes were employed to approximate the intensity derivatives along the propagation direction. The Fourier transform method was implemented for phase reconstruction based on TIE. The reconstructed image was plainly inferior, as shown in FIG. 7C.

Example 7

Figure 8A:
FIG. 8A shows a true phase image.
Figure 8B:
FIG. 8B shows a reconstructed version of the image of FIG. 8A, according to an embodiment of the subject invention.
Figure 8C:
FIG. 8C shows a reconstructed version of the image of FIG. 8A, according to a related art reconstruction method.

The experiment of Example 6 was repeated, using the image of FIG. 8A as the phase contrast image. FIG. 8A shows the true phase image. FIG. 8B shows a reconstructed version of the image of FIG. 8A, reconstructed using a method of the subject invention. FIG. 8C shows a reconstructed version of the image of FIG. 8A, reconstructed using a related art TIE-based reconstruction method. The image of 8A is from Tapfer et al. ("Three-dimensional imaging of whole mouse models: comparing nondestructive X-ray phase-contrast micro-CT with cryotome-based planar epi-illumination imaging," Journal of Microscopy 253(1), 24-30 (2014)). The phase image had 256×238 pixels with a pixel size of 3 μm. The radiation wavelength was set to λ=0.25 Å.

The intensity distribution on the object plane was uniform again. The intensity distribution on the image plane at a propagation distance of 1000 mm was simulated based on Equation (38), with Poisson noise similarly added. The ART-based reconstruction procedure took 5 iterations to generate the phase contrast image shown in FIG. 8B. In the same setting, the phase reconstruction was performed using the TIE-based reconstruction method, as shown in FIG. 8C. These results suggest that the phase imaging method of the subject invention is plainly superior to the TIE-based method.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

T. Davis, D. Gao, T. Gureyev, A. Stevenson, and S. Wilkins, "Phase-contrast imaging of weakly absorbing materials using hard X-rays," Nature, vol. 373, no. 6515, pp. 595-598, 1995.

A. Momose, T. Takeda, Y. Itai, and K. Hirano, "Phase-contrast X-ray computed tomography for observing biological soft tissues," Nature medicine, vol. 2, no. 4, pp. 473-475, 1996.

F. Pfeiffer, T. Weitkamp, O. Bunk, and C. David, "Phase retrieval and differential phase-contrast imaging with low-brilliance X-ray sources," Nature physics, vol. 2, no. 4, pp. 258-261, 2006.

R. Fitzgerald, "Phase-sensitive x-ray imaging," Phys. Today, vol. 53, no. 7, pp. 23-26, 2000.

R. Lewis, "Medical phase contrast x-ray imaging: current status and future prospects," Physics in medicine and biology, vol. 49, no. 16, pp. 3573, 2004.

T. Takeda, A. Momose, K. Hirano, S. Haraoka, T. Watanabe, and Y. Itai, "Human Carcinoma: Early Experience with Phase-Contrast X-ray CT with Synchrotron Radiation—Comparative Specimen Study with Optical Microscopy 1," Radiology, vol. 214, no. 1, pp. 298-301, 2000.

M. Stampanoni, Z. Wang, T. Thüring, C. David, E. Roessl, M. Trippel, R. A. Kubik-Huch, G. Singer, M. K. Hohl, and N. Hauser, "The first analysis and clinical evaluation of native breast tissue using differential phase-contrast mammography," Investigative radiology, vol. 46, no. 12, pp. 801-806, 2011.

A. Momose, W. Yashiro, K. Kido, J. Kiyohara, C. Makifuchi, T. Ito, S. Nagatsuka, C. Honda, D. Noda, and T. Hattori, "X-ray phase imaging: from synchrotron to hospital," Philosophical Transactions of the Royal Society A: Mathematical, Physical and Engineering Sciences, vol. 372, no. 2010, pp. 20130023, 2014.

J. Tanaka, M. Nagashima, K. Kido, Y. Hoshino, J. Kiyohara, C. Makifuchi, S. Nishino, S. Nagatsuka, and A. Momose, "Cadaveric and<i> in vivo</i> human joint imaging based on differential phase contrast by X-ray Talbot-Lau interferometry," Zeitschrift für Medizinische Physik, vol. 23, no. 3, pp. 222-227, 2013.

S. Wilkins, T. Gureyev, D. Gao, A. Pogany, and A. Stevenson, "Phasecontrast imaging using polychromatic hard X-rays," Nature, vol. 384, no. 6607, pp. 335-338, 1996.

D. Chapman, W. Thomlinson, R. Johnston, D. Washburn, E. Pisano, N. Gmür, Z. Zhong, R. Menk, F. Arfelli, and D. Sayers, "Diffraction enhanced xray imaging," Physics in medicine and biology, vol. 42, no. 11, pp. 2015, 1997.

A. Momose, S. Kawamoto, I. Koyama, Y. Hamaishi, K. Takai, and Y. Suzuki, "Demonstration of X-ray Talbot interferometry," Japanese journal of applied physics, vol. 42, no. 7B, pp. L866, 2003.

P. Zhu, K. Zhang, Z. Wang, Y. Liu, X. Liu, Z. Wu, S. A. McDonald, F. Marone, and M. Stampanoni, "Low-dose, simple, and fast grating-based X-ray phase-contrast imaging," Proceedings of the National Academy of Sciences, vol. 107, no. 31, pp. 13576-13581, 2010.

A. Tapfer, M. Bech, A. Velroyen, J. Meiser, J. Mohr, M. Walter, J. Schulz, B. Pauwels, P. Bruyndonckx, and X. Liu, "Experimental results from a preclinical X-ray phase-contrast CT scanner," Proceedings of the National Academy of Sciences, vol. 109, no. 39, pp. 15691-15696, 2012.

G. Wang, H. Yu, and B. De Man, "An outlook on x-ray CT research and development," Medical physics, vol. 35, no. 3, pp. 1051-1064, 2008.

F. L. Pedrotti, L. S. Pedrotti, and L. M. Pedrotti, *Introduction to optics*: Prentice-Hall Englewood Cliffs, 1993.

T. Weitkamp, C. David, O. Bunk, J. Bruder, P. Cloetens, and F. Pfeiffer, "X-ray phase radiography and tomography of soft tissue using grating interferometry," *European Journal of Radiology* 68(3), S13-S17 (2008).

F. Pfeiffer, J. Herzen, M. Wiliner, M. Chabior, S. Auweter, M. Reiser, and F. Bamberg, "Grating-based X-ray phase contrast for biomedical imaging applications," *Zeitschrift Fur Medizinische Physik* 23(3), 176-185 (2013).

A. Momose, T. Takeda, Y. Itai, and K. Hirano, "Phase-contrast X-ray computed tomography for observing biological soft tissues," *Nature Medicine* 2(5), 596-596 (1996).

A. Bravin, P. Coan, and P. Suortti, "X-ray phase-contrast imaging: from pre-clinical applications towards clinics," *Physics in Medicine and Biology* 58(1), R1-R35 (2013).

A. Tapfer, M. Bech, I. Zanette, P. Symvoulidis, S. Stangl, G. Multhoff, M. Molls, V. Ntziachristos, and F. Pfeiffer, "Three-dimensional imaging of whole mouse models: comparing nondestructive X-ray phase-contrast micro-CT with cryotome-based planar epi-illumination imaging," *Journal of Microscopy* 253(1), 24-30 (2014).

J. P. Guigay, "Fourier-Transform Analysis of Fresnel Diffraction Patterns and in-Line Holograms," *Optik* 49(1), 121-125 (1977).

M. R. Teague, "Irradiance Moments—Their Propagation and Use for Unique Retrieval of Phase," *Journal of the Optical Society of America* 72(9), 1199-1209 (1982).

M. R. Teague, "Deterministic Phase Retrieval—a Green-Function Solution," *Journal of the Optical Society of America* 73(11), 1434-1441 (1983).

W. Cong, and G. Wang, "Higher-order phase shift reconstruction approach," *Medical Physics* 37(10), 5238-5242 (2010).

J. P. Guigay, M. Langer, R. Boistel, and P. Cloetens, "Mixed transfer function and transport of intensity approach for phase retrieval in the Fresnel region," *Optics Letters* 32(12), 1617-1619 (2007).

M. Langer, P. Cloetens, J. P. Guigay, and F. Peyrin, "Quantitative comparison of direct phase retrieval algorithms in in-line phase tomography," *Medical Physics* 35(10), 4556-4566 (2008).

X. Z. Wu, and H. Liu, "A general theoretical formalism for X-ray phase contrast imaging," *Journal of X-Ray Science and Technology* 11(1), 33-42 (2003).

M. Soto, and E. Acosta, "Improved phase imaging from intensity measurements in multiple planes," *Applied Optics* 46(33), 7978-7981 (2007).

C. Y. Chou, Y. Huang, D. Shi, and M. A. Anastasio, "Image reconstruction in quantitative X-ray phase-contrast imaging employing multiple measurements," *Optics Express* 15(16), 10002-10025 (2007).

X. Z. Wu, and H. Liu, "Clarification of aspects in in-line phase-sensitive x-ray imaging," *Medical Physics* 34(2), 737-743 (2007).

D. Paganin, *Coherent x-ray optics*, Oxford; New York: Oxford University Press, 2006.

H. Y. Yu, and G. Wang, "Compressed sensing based interior tomography," *Physics in Medicine and Biology* 54(9), 2791-2805 (2009).

J. S. Yang, H. Y. Yu, M. Jiang, and G. Wang, "High-order total variation minimization for interior tomography," *Inverse Problems* 26(3), 035013 (2010).

W. Cong, J. Yang and G. Wang, "Differential phase-contrast interior tomography," *Physics in Medicine and Biology* 57(10), 2905-1914 (2012).

T. Weitkamp, A. Diaz, C. David, F. Pfeiffer, M. Stampanoni, P. Cloetens, and E. Ziegler, "X-ray phase imaging with a grating interferometer," *Optics express*, vol. 13, no. 16, pp. 6296-6304, 2005.

K. Patorski, "I The Self-Imaging Phenomenon and its Applications," *Progress in optics*, vol. 27, pp. 1-108, 1989.

J. Wen, Y. Zhang, and M. Xiao, "The Talbot effect: recent advances in classical optics, nonlinear optics, and quantum optics," *Advances in Optics and Photonics*, vol. 5, no. 1, pp. 83-130, 2013.

J. Azaña, and H. G. De Chatellus, "Angular Talbot effect," *Physical Review Letters*, vol. 112, no. 21, pp. 213902, 2014.

M. V. Berry, and S. Klein, "Integer, fractional and fractal Talbot effects," *Journal of modern optics*, vol. 43, no. 10, pp. 2139-2164, 1996.

T. Thüring, M. Abis, Z. Wang, C. David, and M. Stampanoni, "X-ray phasecontrast imaging at 100 [emsp14] keV on a conventional source," *Scientific Reports*, vol. 4, 2014.

A. Bravin, J. Keyriläinen, M. Fernández, S. Fiedler, C. Nemoz, M.-L. Karjalainen-Lindsberg, M. Tenhunen, P. Virkkunen, M. Leidenius, K. Smitten, P. Sipilä, and P. Suortti, "High-resolution CT by diffraction-enhanced xray imaging: mapping of breast tissue samples and comparison with their histo-pathology," Phys. Med. Biol. 52(8), 2197-2211 (2007).

C. David, J. Bruder, T. Rohbeck, C. Grünzweig, C. Kottler, A. Diaz, O. Bunk, and F. Pfeiffer, "Fabrication of diffraction gratings for hard X-ray phase contrast imaging," Microelectron. Eng. 84(5-8), 1172-1177 (2007).

V. Revol, C. Kottler, R. Kaufmann, I. Jerjen, T. Lüthi, F. Cardot, P. Niedermann, U. Straumann, U. Sennhauser, and C. Urban, "X-ray interferometer with bent gratings: Towards larger fields of view," Nucl. Instrum. Methods Phys. Res., Sect. A 648, S302-S305 (2011).

T. Thüring, "Compact X-ray grating interferometry for phase and dark-field computed tomography in the diagnostic energy range," Diss. Diss., ETH Zürich, Nr. 21321, (2013).

Y. Cohen-Sabban and D. Joyeux, "Aberration-free nonparaxial self-imaging," J. Opt. Soc. Am. 73(5), 707 (1983).

W. D. Montgomery, "Self-Imaging Objects of Infinite Aperture," J. Opt. Soc. Am. 57(6), 772 (1967).

M. Abramowitz, I. A. Stegun, and D. Miller, Handbook of Mathematical Functions With Formulas, Graphs and Mathematical Tables (Courier Corporation, 1965).

S. Silver and W. K. Saunders, "The external field produced by a slot in an infinite circular cylinder," J. Appl. Phys. 21(2), 153-158 (1950).

J. A. Stratton, Electromagnetic Theory (John Wiley & Sons, 2007).

What is claimed is:
1. An X-ray phase-contrast imaging (PCI) system, comprising:
an X-ray source;
a detector;
a first grating disposed between the X-ray source and the detector; and
a second grating disposed between the first grating and the detector,
wherein the first grating is a quasi-periodical phase grating such that a period of the first grating varies across the first grating and changes equally in both lateral directions.

2. The system according to claim 1, wherein the second grating is an analyzer grating.

3. The system according to claim 1, wherein the detector is flat.

4. The system according to claim 3, wherein the detector is a flat detector array.

5. The system according to claim 1, wherein the second grating is flat.

6. The system according to claim 1, wherein the first grating is curved.

7. The system according to claim 6, wherein the first grating is a cylindrical grating or a spherical grating.

8. The system according to claim 1, wherein the detector is flat,
wherein the second grating is flat, and
wherein the first grating is a cylindrical grating or a spherical grating.

9. The system according to claim 1, further comprising a source grating disposed between the X-ray source and the first grating.

10. The system according to claim 9, wherein the source grating is a cylindrical grating or a spherical grating.

11. The system according to claim 1, wherein the period of the first grating varies the same way in both lateral directions as an angle is varied positively or negatively by the same amount from a point on the first grating where X-rays from the X-ray source are centered during imaging.

12. A method of performing X-ray phase-contrast imaging, comprising:
providing the imaging system according to claim 1;
positioning an object to be imaged between the X-ray source and the first grating; and
imaging the object using the system.

13. The method according to claim 12, wherein the detector is flat,
wherein the second grating is flat, and
wherein the first grating is a cylindrical grating or a spherical grating.

14. The method according to claim 13, wherein the second grating is an analyzer grating.

15. The method according to claim 13, wherein the imaging system further comprises a source grating disposed between the X-ray source and the first grating,
wherein the source grating is a cylindrical grating or a spherical grating,
and wherein the object is positioned between the source grating and the first grating for imaging of the object.

16. The system according to claim 1, wherein the first grating is disposed closer to the detector than it is to the X-ray source such that the system is configured so the first grating is disposed between the detector and an object to be imaged.

* * * * *